US010111651B2

(12) United States Patent
Deitch et al.

(10) Patent No.: US 10,111,651 B2
(45) Date of Patent: Oct. 30, 2018

(54) SYSTEM AND METHOD OF ANCHORING SUPPORT MATERIAL TO TISSUE

(71) Applicant: Coloplast A/S, Humlebaek (DK)

(72) Inventors: Sarah J. Deitch, Minneapolis, MN (US); Michael M. Witzmann, Shoreview, MN (US)

(73) Assignee: Coloplast A/S, Humnlebaek (DK)

( * ) Notice: Subject to any disclaimer, the term of this patent is extended or adjusted under 35 U.S.C. 154(b) by 1011 days.

(21) Appl. No.: 14/050,361

(22) Filed: Oct. 10, 2013

(65) Prior Publication Data
US 2014/0128914 A1 May 8, 2014

Related U.S. Application Data

(60) Provisional application No. 61/721,563, filed on Nov. 2, 2012, provisional application No. 61/884,143, filed on Sep. 30, 2013.

(51) Int. Cl.
*A61B 17/04* (2006.01)
*A61B 17/06* (2006.01)

(52) U.S. Cl.
CPC .. *A61B 17/0401* (2013.01); *A61B 2017/0409* (2013.01); *A61B 2017/0412* (2013.01);
(Continued)

(58) Field of Classification Search
CPC ........ A61B 17/0401; A61B 2017/0464; A61B 2017/0419; A61B 2017/0409;
(Continued)

(56) References Cited

U.S. PATENT DOCUMENTS 2,738,790 A  3/1956  Todt et al.
4,009,711 A  3/1977  Uson
(Continued)

FOREIGN PATENT DOCUMENTS

EP  1484022 A2  12/2004
FR  2973217 A1  10/2012
(Continued)

OTHER PUBLICATIONS

OA dated Jun. 4, 2015 in U.S. Appl. No. 14/050,367.
(Continued)

*Primary Examiner* — Julian W Woo
*Assistant Examiner* — Tin Nguyen
(74) *Attorney, Agent, or Firm* — Coloplast Corp. Coloplast A/S; Nick Baumann

(57) ABSTRACT

A method of anchoring a support material to tissue includes forming an incision in a urogenital triangle of a patient for access to a pelvis of the patient; inserting a body portion of an anchor into a lumen in a cannula and having a spine portion of the anchor extending radially out of a wall of the cannula; and inserting a leading end of the cannula and the anchor into the incision. The method includes pushing the leading end of the cannula into periosteum tissue of the pelvis; engaging the spine portion of the anchor with the periosteum tissue; withdrawing the leading end of the cannula from the incision and leaving the anchor engaged in the periosteum tissue; and securing the support material to a suture that is attached to the anchor. The method includes delivering the support material through the incision to the pelvis.

17 Claims, 30 Drawing Sheets

(52) U.S. Cl.
CPC .............. *A61B 2017/0419* (2013.01); *A61B 2017/0427* (2013.01); *A61B 2017/0464* (2013.01); *A61B 2017/06176* (2013.01)

(58) Field of Classification Search
CPC .. A61B 2017/06176; A61B 2017/0427; A61B 2017/0412; A61F 2/0063; A61F 2/0045; A61F 2/005; A61F 2002/0072; A61F 2002/0068
See application file for complete search history.

(56) References Cited

U.S. PATENT DOCUMENTS

| | | | |
|---|---|---|---|
| 5,230,694 A | 7/1993 | Rosenblum | |
| 5,284,141 A | 2/1994 | Eibling | |
| 5,899,909 A | 5/1999 | Claren et al. | |
| 5,934,283 A | 8/1999 | Willem et al. | |
| 6,042,534 A | 3/2000 | Gellman et al. | |
| 6,050,937 A | 4/2000 | Benderev | |
| 6,102,886 A | 8/2000 | Lundquist et al. | |
| 6,200,330 B1 | 3/2001 | Benderev et al. | |
| 6,273,852 B1 | 8/2001 | Lehe et al. | |
| 6,302,840 B1 | 10/2001 | Benderev | |
| 6,328,686 B1 | 12/2001 | Kovac | |
| 6,491,703 B1 | 12/2002 | Ulmsten | |
| 6,502,578 B2 | 1/2003 | Raz et al. | |
| 6,638,211 B2 | 10/2003 | Suslian et al. | |
| 6,666,817 B2 | 12/2003 | Li | |
| 6,685,626 B2 | 2/2004 | Wironen | |
| 6,808,486 B1 | 10/2004 | O Donnell | |
| 6,884,212 B2 | 4/2005 | Thierfelder et al. | |
| 6,953,428 B2 | 10/2005 | Gellman et al. | |
| 7,083,637 B1 | 8/2006 | Tannhauser | |
| 7,131,943 B2 | 11/2006 | Kammerer | |
| 7,204,802 B2 | 4/2007 | De Leval | |
| 7,393,319 B2 | 7/2008 | Merade et al. | |
| 7,431,690 B2 | 10/2008 | Merade et al. | |
| 7,527,588 B2 | 5/2009 | Zaddem et al. | |
| 7,559,885 B2 | 7/2009 | Merade et al. | |
| 7,878,969 B2 | 2/2011 | Chu et al. | |
| 8,029,435 B2 | 10/2011 | Merade et al. | |
| 8,128,554 B2 | 3/2012 | Browning | |
| 8,182,412 B2 | 5/2012 | Browning | |
| 8,182,413 B2 | 5/2012 | Browning | |
| 8,469,877 B2 | 6/2013 | Browning | |
| 2001/0031973 A1 | 10/2001 | Nobles et al. | |
| 2002/0028980 A1 | 3/2002 | Thierfelder et al. | |
| 2002/0099260 A1 | 7/2002 | Suslian et al. | |
| 2002/0128670 A1 | 9/2002 | Ulmsten et al. | |
| 2002/0161382 A1 | 10/2002 | Neisz et al. | |
| 2002/0188169 A1 | 12/2002 | Kammerer et al. | |
| 2003/0023137 A1 | 1/2003 | Gellman | |
| 2003/0023138 A1 | 1/2003 | Luscombe | |
| 2003/0045774 A1 | 3/2003 | Staskin et al. | |
| 2003/0171644 A1 | 9/2003 | Anderson et al. | |
| 2003/0176762 A1 | 9/2003 | Kammerer | |
| 2003/0212305 A1 | 11/2003 | Anderson et al. | |
| 2003/0216814 A1 | 11/2003 | Siegel et al. | |
| 2004/0002734 A1 | 1/2004 | Fallin | |
| 2004/0039453 A1 | 2/2004 | Anderson et al. | |
| 2004/0087970 A1 | 5/2004 | Chu et al. | |
| 2004/0143152 A1 | 7/2004 | Grocela | |
| 2004/0243178 A1 | 12/2004 | Haut et al. | |
| 2004/0249240 A1 | 12/2004 | Goldmann et al. | |
| 2004/0249473 A1 | 12/2004 | Delorme et al. | |
| 2005/0004576 A1* | 1/2005 | Benderev ........... A61B 17/0401 606/300 | |
| 2005/0027160 A1 | 2/2005 | Siegel et al. | |
| 2005/0085688 A1 | 4/2005 | Girard et al. | |
| 2005/0101834 A1 | 5/2005 | Merade | |
| 2005/0240076 A1 | 10/2005 | Neisz et al. | |
| 2006/0004246 A1 | 1/2006 | Selikowitz | |
| 2006/0058575 A1 | 3/2006 | Zaddem et al. | |
| 2006/0122457 A1 | 6/2006 | Kovac et al. | |
| 2006/0134159 A1 | 6/2006 | Nicita | |
| 2006/0205995 A1 | 9/2006 | Browning | |
| 2006/0229596 A1 | 10/2006 | Weiser et al. | |
| 2006/0247490 A1 | 11/2006 | Merade et al. | |
| 2006/0287571 A1 | 12/2006 | Gozzi et al. | |
| 2007/0032695 A1 | 2/2007 | Weiser | |
| 2007/0049791 A1 | 3/2007 | Merade et al. | |
| 2007/0055095 A1 | 3/2007 | Chu et al. | |
| 2008/0009665 A1 | 1/2008 | Merade et al. | |
| 2008/0076963 A1 | 3/2008 | Goria | |
| 2008/0177132 A1 | 7/2008 | Alinsod et al. | |
| 2008/0210247 A1 | 9/2008 | De Leval | |
| 2008/0300607 A1 | 12/2008 | Meade et al. | |
| 2009/0012351 A1 | 1/2009 | Anderson et al. | |
| 2009/0048479 A1 | 2/2009 | Goria | |
| 2009/0171142 A1 | 7/2009 | Chu | |
| 2009/0247816 A1 | 10/2009 | Merade et al. | |
| 2010/0081866 A1 | 4/2010 | Goddard et al. | |
| 2010/0130814 A1 | 5/2010 | Dubernard | |
| 2010/0191038 A1 | 7/2010 | Kubalak et al. | |
| 2010/0197998 A1 | 8/2010 | Comiter et al. | |
| 2010/0197999 A1 | 8/2010 | Moschel | |
| 2010/0198004 A1 | 8/2010 | Moschel et al. | |
| 2011/0022061 A1 | 1/2011 | Orphanos | |
| 2011/0077457 A1 | 3/2011 | Deitch | |
| 2011/0144417 A1 | 6/2011 | Jagger et al. | |
| 2011/0237878 A1* | 9/2011 | Browning .......... A61B 17/0469 600/37 |
| 2011/0245850 A1 | 10/2011 | van der Burg et al. | |
| 2012/0022317 A1 | 1/2012 | Merade et al. | |
| 2012/0101524 A1 | 4/2012 | Bennett | |
| 2012/0149974 A1 | 6/2012 | Comiter et al. | |
| 2012/0165603 A1 | 6/2012 | Comiter et al. | |
| 2012/0259169 A1 | 10/2012 | Merade et al. | |
| 2013/0046132 A1 | 2/2013 | Buie et al. | |
| 2013/0046133 A1 | 2/2013 | Buie et al. | |
| 2013/0231524 A1 | 9/2013 | Merade et al. | |
| 2014/0039244 A1 | 2/2014 | Browning | |
| 2014/0039248 A1 | 2/2014 | Browning | |
| 2014/0051917 A1 | 2/2014 | Browning | |
| 2014/0194675 A1 | 7/2014 | Merade et al. | |
| 2014/0194676 A1 | 7/2014 | Comiter et al. | |

FOREIGN PATENT DOCUMENTS

| | | |
|---|---|---|
| JP | 2004522470 T2 | 7/2004 |
| JP | 2004525483 T2 | 8/2004 |
| RU | 2185779 C2 | 7/2002 |
| RU | 2243729 C1 | 1/2005 |
| RU | 2275883 C2 | 5/2006 |
| WO | 03002027 A1 | 1/2003 |
| WO | 2003075792 A1 | 9/2003 |
| WO | 03096929 A1 | 11/2003 |
| WO | 2003094784 A2 | 11/2003 |
| WO | 2004012579 A2 | 2/2004 |
| WO | 2004012626 A1 | 2/2004 |
| WO | 2004045457 A1 | 6/2004 |
| WO | 2004091442 A2 | 10/2004 |
| WO | 2005027786 A1 | 3/2005 |
| WO | 2005110243 A2 | 11/2005 |
| WO | 2006020530 A2 | 2/2006 |
| WO | 2006041861 A2 | 4/2006 |
| WO | 2007014241 A1 | 2/2007 |
| WO | 2007118260 A1 | 10/2007 |
| WO | 07137226 A2 | 11/2007 |
| WO | 2008152435 A1 | 12/2008 |
| WO | 2010093421 A2 | 8/2010 |
| WO | 2011106419 A1 | 9/2011 |

OTHER PUBLICATIONS

Chon, J.; D. Bodell; K. Kobashi; G. Leach, Results of the Transvaginal Cadaveric Prolapse Repair with Sling (CAP); p. 150, 2002.

Kobashi, K; S.Mee; G. Leach; A New Technique for Cystocele Repair and Transvaginal Sling: The Cadaverix Prolaps Repair and Sling (CaPS); Elsevier Science Inc.; Dec. 2000; pp. 9-14.

Kobashi, K. and Govier, F.; The Use of Solvent-Dehydrated Cadaveric Fascia Lata (TUTOPLAST) in Slings and Cystocele Repairs; the

(56) References Cited

OTHER PUBLICATIONS

Virginia Mason Experience; Virginia Mason Medical Center; J. Urol 2002; p. 151.
Almeida, Silvio H.M. et al; Use of Cadaveric Fascia Lata to Correct Grade IV Cystocele; Official Journal of the Brazilian Society of Urology, State University of Londrian, Parana, Brazil; pp. 48-52, Feb. 2003.
Moir, The Journal of Obstetrics and Gyneacolog, Jan. 1968.
Shaw, British Medical Journal, Jun. 1949.
Ulmsten et al, International Urogynecology Journal, vol. 7, 1996.
Office Action dated Sep. 1, 2016 in U.S. Appl. No. 14/050,352.
Office Action dated Nov. 3, 2017 in U.S. Appl. No. 14/050,352.

\* cited by examiner

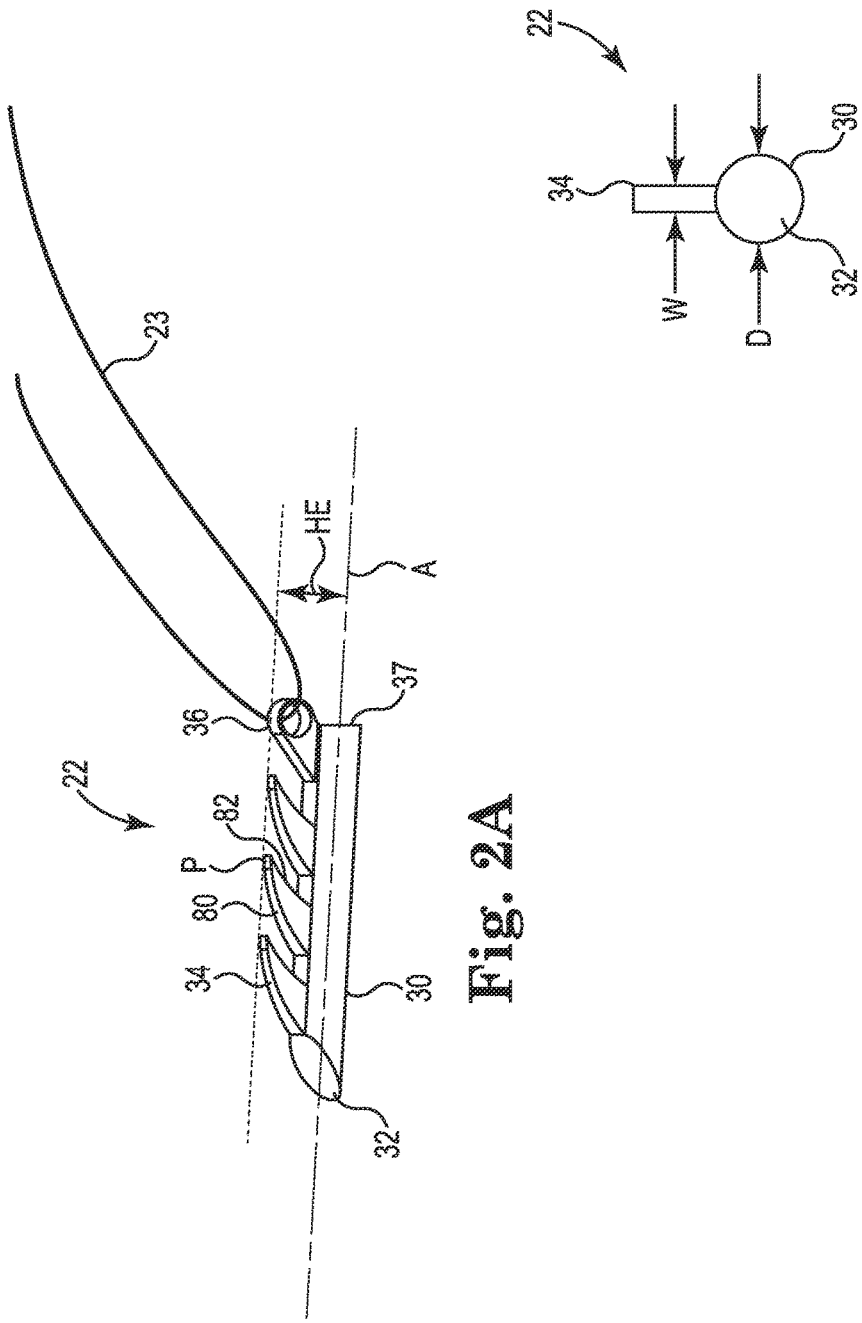

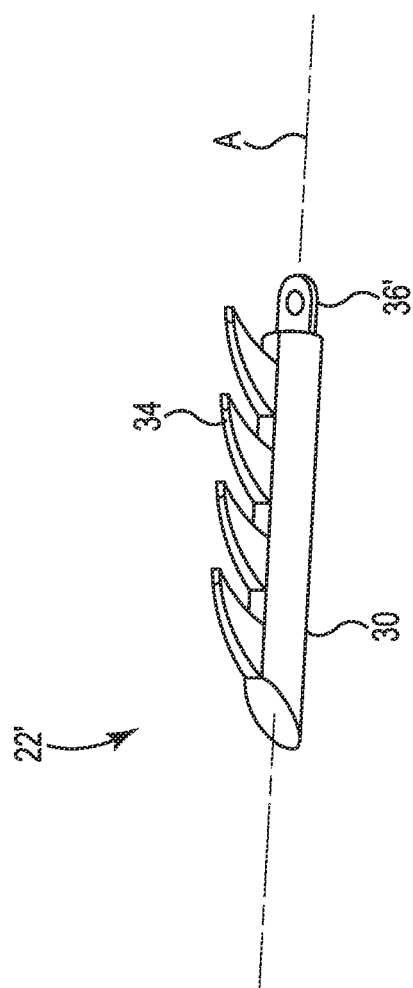

SYSTEM AND METHOD OF ANCHORING SUPPORT MATERIAL TO TISSUE

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon is unable to see the suture site. In such a case, the surgeon will digitally palpate with a finger to locate a landmark within the intracorporeal site, and then deliver the suture near at or near the landmark. Tying of the suture inside the patient at the intracorporeal site can be challenging since the surgeon is unable to see the site.

Improved suturing instruments and improved methods of delivering sutures would be welcomed by the surgical staff.

SUMMARY

One aspect provides a surgical system including an anchor and an introducer provided to deliver the anchor into tissue. The anchor includes a body having a pointed leading end that is configured to pierce the tissue, a spine projecting radially away from the body and having a width and a height configured to allow the spine to engage with the tissue, an eyelet attached to a trailing end of the body, and a length of suture attached to the eyelet. The introducer includes a cannula with a pointed distal end, an opening formed in the cannula that is sized to receive the body of the anchor, and a slot formed in a wall of the cannula at a distal end portion of the cannula and sized to receive the width of the spine. When readied for use, the anchor is secured in the introducer with the body of the anchor inserted into the opening of the cannula with the pointed leading end of the body located proximal of the pointed distal end of the cannula. The spine of the anchor is inserted into the slot of the cannula such that the anchor does not rotate relative to the cannula.

One aspect provides a method of anchoring a support material to tissue. The method includes forming an incision in a urogenital triangle of a patient for access to a pelvis of the patient; inserting a body portion of an anchor into a lumen in a cannula and having a spine portion of the anchor extending radially out of a wall of the cannula; and inserting a leading end of the cannula and the anchor into the incision. The method additionally includes pushing the leading end of the cannula into periosteum tissue of the pelvis and engaging the spine portion of the anchor with the periosteum tissue. The method further includes withdrawing the leading end of the cannula from the incision and leaving the anchor engaged in the periosteum tissue; and securing the support material to a suture that is attached to the anchor. The method includes delivering the support material along the suture and through the incision and into the patient to the pelvis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2A is a perspective view of the anchor illustrated in FIG. 1.

FIG. 2B is an end view of the anchor.

FIG. 2C is a perspective view of one embodiment of an anchor for the surgical system illustrated in FIG. 1.

DETAILED DESCRIPTION

Figure 1:
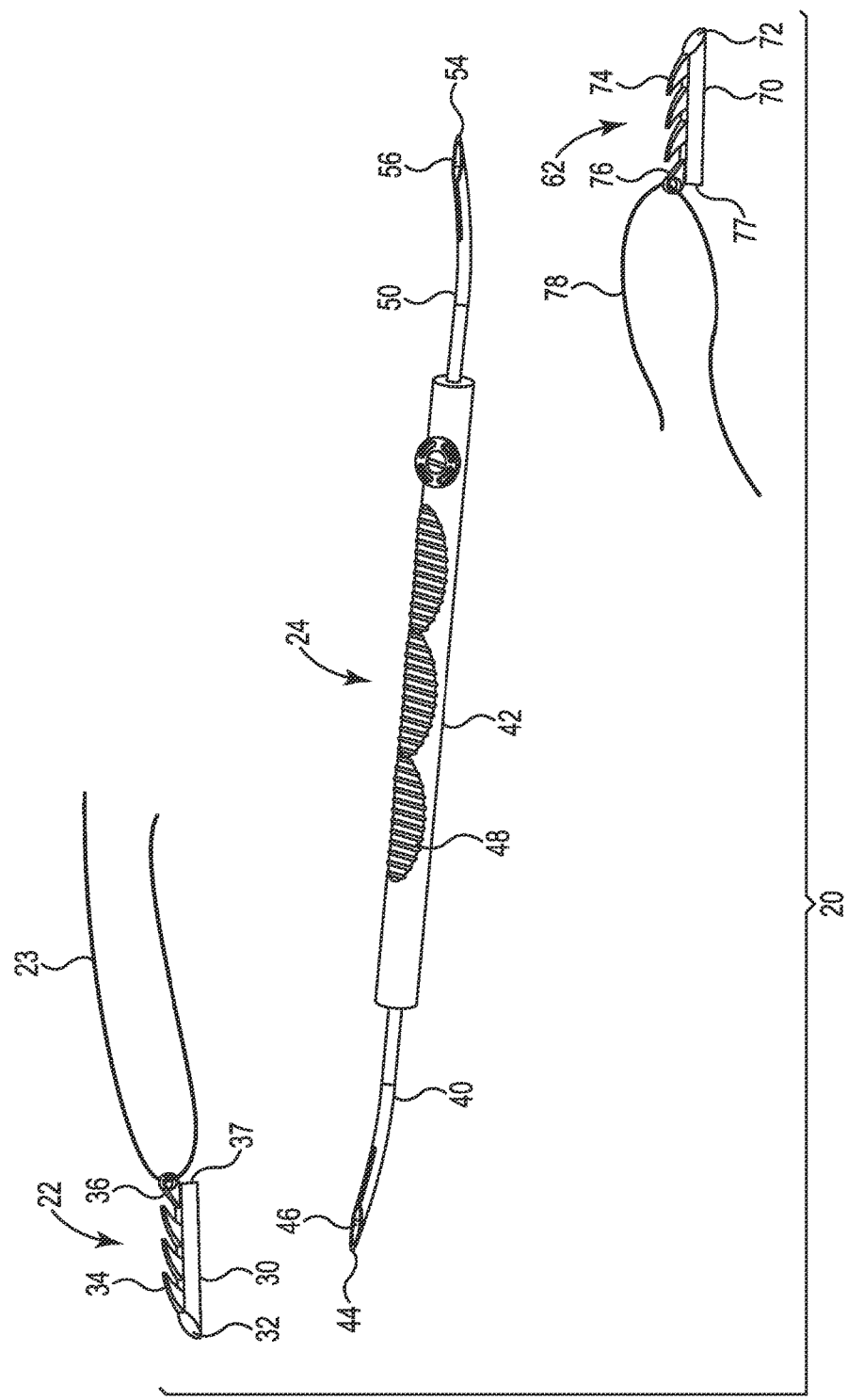
FIG. 1 is a perspective view of one embodiment of a surgical system including an anchor that is insertable into a cannula of an introducer.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The features of the various exemplary embodiments described in this application are suitable and intended to be combined with each other, unless specifically noted otherwise.

Anterior means "forward" or "front," and posterior means "rearward" or "back." Relative to surfaces of an organ in the human body, an anterior surface of an instrument inserted into the organ will be oriented forward toward the belly and a posterior surface will be oriented rearward toward the spine.

End means an end most location and end portion means that segment adjacent to and near the end of an object. For example, two opposing ends of an object are each equidistant from a mid-point of the object and between the mid-point and each end of the object is an end portion of the object.

Embodiments provide a surgical system including an introducer that is configured to deliver an anchor to an intracorporeal tissue site. The introducer includes a cannula that allows placement of an anchor at a landmark in tissue deep within an incision site, which may be out of the field of vision of the surgeon. The anchor is configured to be secured within the cannula so that it does not rotate or fall out of the cannula during insertion into the tissue. A length of suture is provided that is attached to the anchor, where the suture may be tied or otherwise terminated to itself outside of the incision site and then subsequently directed to the intracorporeal landmark.

Some incontinence treatment devices have several arms, including some form of arms that traverse the obturator foramen (called transobturator arms) and other arms that are implanted anterior to the pubic bone (called pre-pubic arms). A first set of tools is used to place the transobturator arms and a second, different set of tools is used to place the pre-pubic arms. The pre-pubic arms are tunneled anterior to the pelvis and exit the skin of the abdomen.

In contrast, embodiments of the system described in this specification provide a support with two transobturator arms and a system to attach a portion of the support directly and efficiently to the periosteum tissue. The system obviates the use of additional pre-pubic arms and additional tools that tunnel the pre-pubic arms under the skin. The system is easier to implant compared to a four arm or six arm support, and reduces the amount of time that the patient is in the operating room.

One approach to treating urinary incontinence places a support inferior to the urethra and directs arms upward from the support alongside the bladder along a U-shaped pathway. A significant advance over the U-shaped pathway was provided by Dr. Emmanuel Delorme as described in his U.S. Pat. No. 6,638,211 and included placing arms of a support through the obturator foramen along a V-shaped pathway. This application provides another advance in supporting the pelvic anatomy by recognizing that support material can be robustly attached to the periosteum tissue through the use of an anchoring system. The anchoring system allows the surgeon to place the support inside of the patient and directly fixate the support to periosteum tissue that is present over the exterior of the bones. This approach does away with needles and other tools that tunnel the arms of a support through tissue. The anchoring system described in this application is compatible with a true single (only one) incision formed in the patient.

FIG. 1 is a perspective view of one embodiment of a surgical system 20. The surgical system 20 (system 20) includes an anchor 22 attached to a length of suture 23 and an introducer 24 adapted to deliver the anchor 22 to an intracorporeal landmark. The anchor 22 is sized to be inserted into the introducer 24, and the introducer 24 is sized to be inserted through a single incision to push or direct the anchor 22 into tissue. The suture 23 trails behind the anchor 22 and is available for subsequent ligation of the tissue, or for subsequent attachment of a support to the tissue.

The anchor 22 includes a body 30 having a pointed leading end 32 that is configured to pierce tissue, a spine 34 projecting radially away from the body 30 and configured to engage with or anchor to tissue, and an eyelet 36 attached to a trailing end 37 of the body 30. The length of suture 23 is inserted through the eyelet 36.

The introducer 24 includes a cannula 40 extending from a handle 42. The cannula 40 has a pointed distal end 44 and an opening 46 formed in the cannula 40. The opening 46 or lumen 46 is sized to receive the body 30 of the anchor 22. The handle 42 includes a gripping surface 48 formed on at least one side of the handle 42. It is acceptable to provide the handle 42 with several gripping surfaces or with no gripping surfaces. During a suturing procedure, the anchor 22 is loaded into the opening 46 of the cannula 40 and the surgeon grips the handle 42 and directs the pointed distal end 44 of the cannula to a targeted tissue landmark. Force delivered to the handle 42 in a distal direction will drive the pointed distal end 44 of the cannula 40 into the tissue, such that a subsequent withdrawal of the introducer 24 in a proximal direction will allow the introducer 24 to exit the tissue. The spine 34 (and in some cases the eyelet 36) engages with the tissue, thus leaving the anchor 22 engaged with and deposited in the tissue after the cannula 40 is withdrawn.

In one embodiment, the introducer 24 includes a pair of cannulas, including a second cannula 50 having a pointed distal end 54 and an opening 56 formed in the cannula 50. The second cannula 50 is provided to receive a second, separate anchor. With this in mind, a second anchor 62 is provided having a body 70 having a pointed leading end 72, a spine 74 projecting radially from the body 70, an eyelet 76 attached to a trailing end 77 of the body 70, and a second length of suture 78 attached to the eyelet 76. In this embodiment, the introducer 24 is operable to deliver the first anchor 22 out of the first cannula 40 and to subsequently deliver the second anchor 62 out of the second cannula 50. The gripping surface 48 is configured to allow the translation or rotation of the instrument to selectively move each of the cannulas 40, 50 to a forward facing proximal position.

FIG. 2A is a perspective view of the anchor 22 and FIG. 2B is an end view of the anchor 22. The anchor 22 includes multiple spines 34 extending from the body 30. In one embodiment, the spines 34 project radially away from a center longitudinal axis A of the body 30, with each spine 34 shaped as a shark fin having a curved leading edge 80 that meets with a curved trailing edge 82 at a point P. The curved leading edge 80 is oriented to diverge away from the pointed leading end 32 of the body 30 to allow the anchor 22 to glide into tissue and prevent the anchor from pulling out of the tissue. Although three spines 34 and one eyelet 36 are illustrated, the anchor 22 is also suitably provided with a single spine 34 and one eyelet 36. The anchor 22 is also suitably provided with more than three spines 34.

The eyelet 36 projects radially away from the center longitudinal axis A of the body 30 and as such is also configured to engage with tissue. For example, the eyelet 36 is provided with a height HE that is substantially equal to the height of the spines 34 (the distance that the point P is away from the center axis A). The eyelet has a width substantially equal to the width W of the spine 34.

The body 30 of the anchor 22 is substantially circular in lateral cross-section (FIG. 2B). The anchor 22 is configured to slide in an entry direction through the tissue, and is shaped to prevent withdrawal of the anchor 22 in the direction that is opposite of the entry direction. The curved leading edge 80 of the shark fin shape of the spines 34 facilitate the easy sliding of the anchor 22 through the tissue in the entry direction, and the curved trailing edge 82 of the spines 34 configure the anchor to resist being pulled out of the tissue in the direction that is opposite of the entry direction. In one embodiment, the body 30 of the anchor 22 has a diameter D, and the spine 34 has a width W that is less than about 25% of the diameter D (FIG. 2B).

FIG. 2C is a perspective view of one embodiment of an anchor 22' provided with an eyelet 36' that is disposed on the center longitudinal axis A of the body 30. The spines 34 of the anchor 22' are provided to engage with tissue, and the eyelet 36' is streamlined to follow the body 30 into the tissue channel that is formed when the anchor 22' is driven into the tissue by the introducer 24 (FIG. 1).

Figure 3:
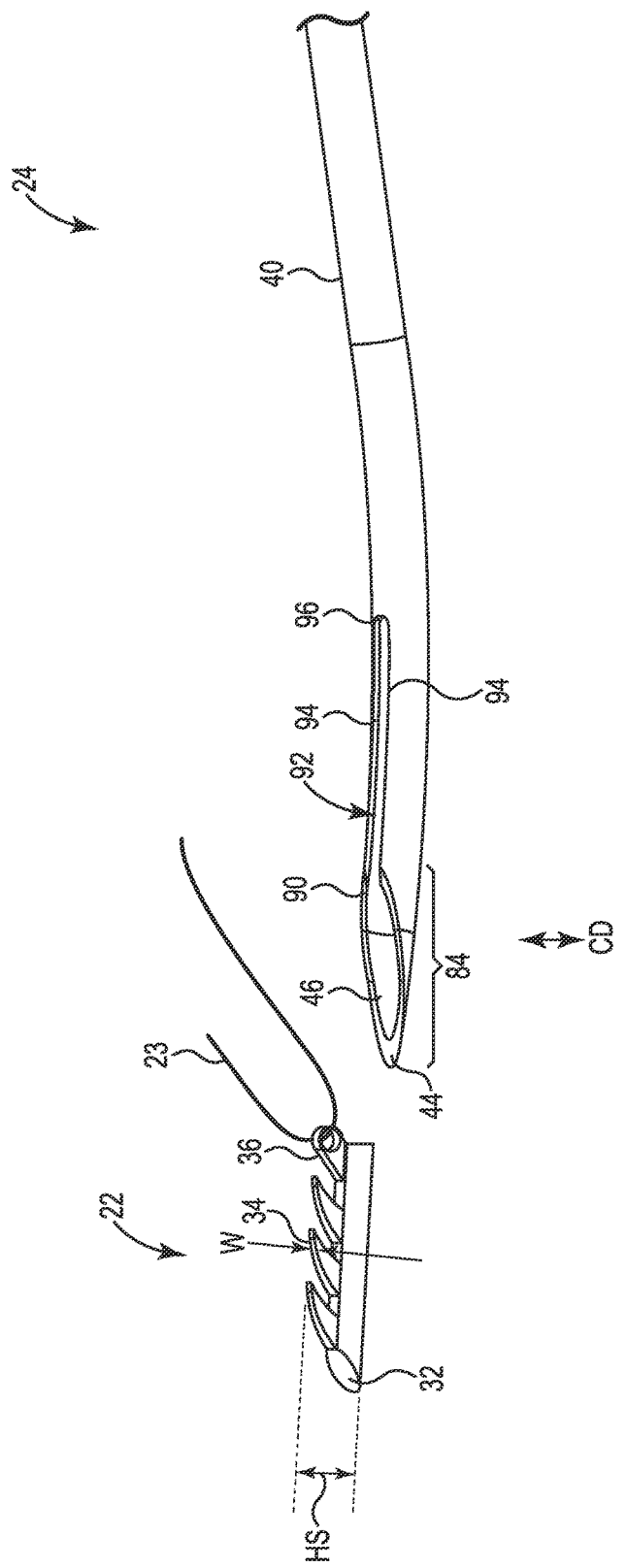
FIG. 3 is a perspective view of the anchor outside of the cannula illustrated in FIG. 1.
Figure 4:
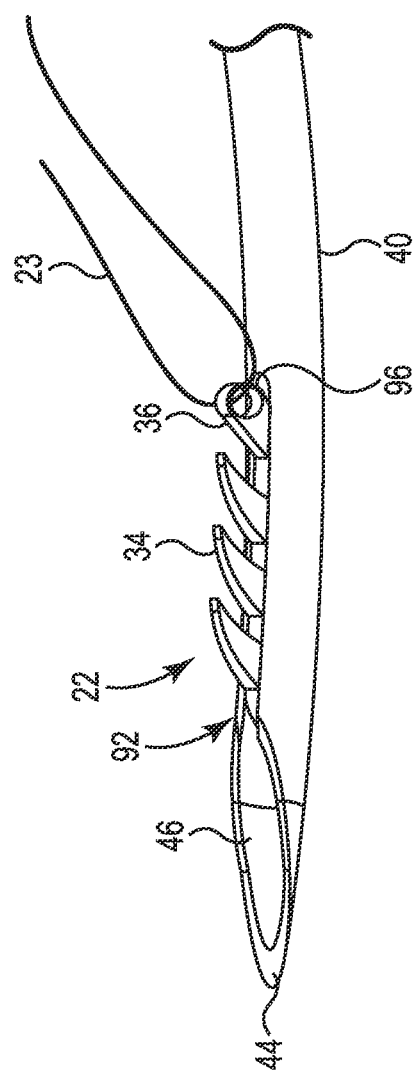
FIG. 4 is a perspective view of the anchor inserted into a lumen of the cannula illustrated in FIG. 1.

FIG. 3 is a perspective view of the anchor 22 positioned for insertion into the cannula 40 of the introducer 24 and FIG. 4 is a perspective view of the anchor 22 inserted into the cannula 40. The body 30 of the anchor 22 is sized to slide into the opening 46 (also called a lumen 46) of the cannula 40 with the spine 34 projecting out of the cannula 40. With reference to FIG. 3, the inside diameter of the lumen 46 of the cannula 40 provides a cannula diameter CD, and the spine 34 has a height HS that is greater than the cannula diameter CD. The height HS the spine 34 is at least 5% greater than the cannula diameter CD. For example, the height HS of the spine 34 is in the range of 5-100% greater than the cannula diameter CD.

It is acceptable for the height HE (FIG. 2A) of the eyelet 36 to be equal to the height HS of the spine 34. It is also acceptable for the height HE (FIG. 2A) of the eyelet 36 to be different from and not equal to the height HS of the spine 34.

The cannula 40 includes a tapered distal end portion 84 that tapers to the pointed distal end 44, where the tapered distal end portion 84 provides the cannula 40 with a needle-like point adapted for insertion through tissue. In some applications, the pointed distal end 44 of the cannula 40 is sharp and needle-like and is so configured to enter the periosteum tissue covering a boney surface and glide under the periosteum tissue and over the bone. In this manner, the cannula is configured to deliver the anchor 22 between the periosteum tissue and the bone.

The cannula 40 has a wall 90 that forms or defines the lumen 46 and a slot 92 formed through the wall 90. The slot 92 is proximal of the tapered distal end portion 84 and extends through the wall 90 to communicate with the lumen 46. The slot 92 includes a pair of opposed longitudinal side edges 94 that extend from a proximal lateral edge 96 in a distal direction to the distal end portion 84. The width of the slot between the longitudinal side edges 94 is sized to receive the width W of the spines 34. The cannula diameter CD is sized to receive the diameter D (FIG. 2B) of the body 30 of the anchor 22.

With reference to FIG. 4, when the anchor 22 is loaded into the cannula 40, the pointed leading end 32 of the body 30 is located proximal of the pointed distal end 44 of the cannula 40, and the spines 34 and the eyelet 36 extend outside of the cannula 40 and are positioned to engage with tissue during implantation of the anchor 22. The proximal lateral edge 96 of the slot 92 is positioned to push against the eyelet 36 and drive the anchor 22 into the tissue. The opposed longitudinal side edges 94 of the slot 92 provide a stanchion that restrains the spines 34 and prevents the anchor 22 from rotating relative to the cannula 40. The spines 34 and the eyelet 36 slide in a longitudinal direction relative to the slot 92 to allow the cannula 40 to be removed from the tissue while leaving the anchor 22 implanted.

Suitable materials for fabricating the anchor 22 include plastics, or metal, or sintered material. One suitable material for fabricating the anchor 22 is polypropylene. Another suitable material for fabricating the anchor 22 is a bioabsorbable polymer that configures the anchor 22 to be absorbed into the body over a period of several weeks.

Suitable materials for fabricating the length of suture 23 include bio-inert components that do not bioabsorb, or bioabsorbable components that are configured to be absorbed or resorbed by the body. One suitable material for fabricating the length of suture 23 is polypropylene. Other suitable materials for fabricating the length of suture 23 include dissolvable sutures available from Ethicon™, a J&J Company located in Somerville, N.J., and include Monocryl™ (polyglycaprone 25) sutures, coated Vicryl™ (polyglactin 910) sutures, Ethicon Plus™ Sutures, or polydioxanone sutures as examples.

Suitable materials for fabricating the cannula 40 and include plastics or metal. One suitable material for fabricating the cannula 40 is stainless steel. Other suitable materials are acceptable.

With reference to FIG. 1, the anchor 22 is useful for fixating a support material within a patient's body. The introducer 24 is sized to place the anchors 22 through a single incision and into the periosteum tissue that covers the pubic bone, examples of which are described below.

Figure 5:
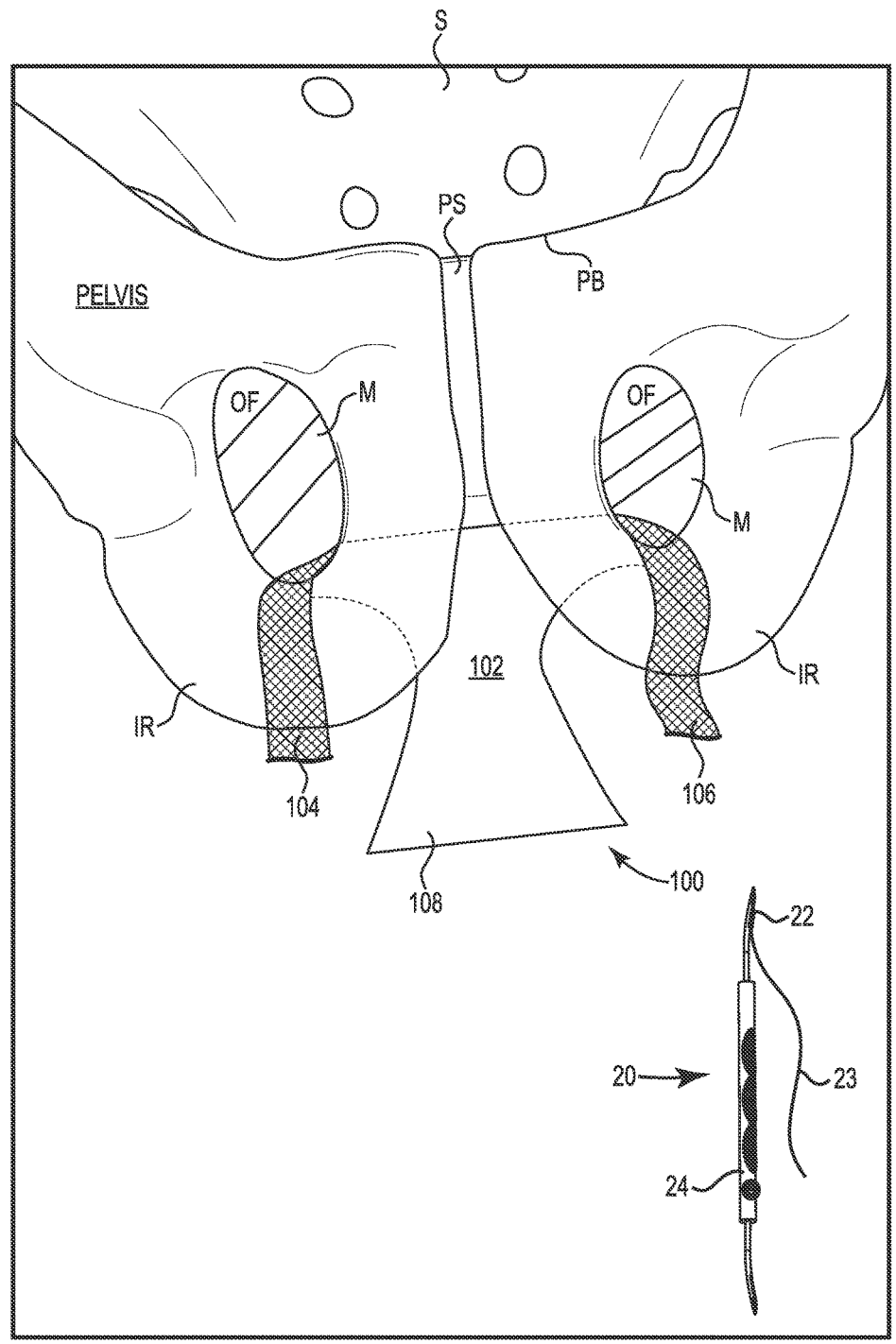
FIG. 5 is a schematic view of one embodiment of the surgical system provided to anchor a support material to tissue of the human body, with the support material having an arm inserted through each of two obturator foramen of the pelvis.

FIG. 5 is a schematic view of one embodiment of a support 100 attachable to a pelvis of a patient. FIG. 5 provides an anterior view of the pelvis with the sacrum S located in a posterior portion of the view, with the pubic symphysis PS centered relative to the pubic bone PB, and an obturator foramen OF on each bilateral side of the pelvis. Each obturator foramen OF provides an opening or a window that is covered by a membrane M. Nerves and arteries traverse the upper reaches of the obturator foramen OF. The membrane M generally includes several layers of muscle and at least one layer of ligament-like tissue that connects the muscles in the membrane M to the pelvis. The ischial pubic ramus IR is located inferior to the pubic bone PB and the obturator foramen OF.

The support 100 is provided to elevate and compress the male urethra and includes a body 102, a first arm 104 extending from the body 102, a second arm 106 extending from the body 102, and a pre-pubic portion 108 that is oriented in a generally orthogonal position relative to the arms 104, 106. The illustrated embodiment is a two-arm device.

Suitable materials for fabricating the support 100 include porous materials that allow tissue ingrowth throughout the support structure to anchor the support 100 in the body after implantation and healing. Suitable such porous materials include autograft material (the patient's own tissue), allograft material (tissue from a cadaver), xenograft material (tissue from another species), or synthetic materials such as woven fabrics, meshes, nonwoven fabrics, meshes, fibrillated fibers, or spun and fibrillated fibers that are provided with voids (pores) configured to allow tissue ingrowth into the support 100. The pores are generally larger, on average, than 75 μm.

The support 100 is attached to the pelvis with each arm 104, 106 inserted into one of the respective obturator foramen OF, and with the pre-pubic portion 108 attached to the periosteum tissue that lines the exterior of the pubic bone PB. The following surgical procedure is one example of the suitable implantation of the support 100 into a male patient.

The patient is positioned on a surgical operating table in a lithotomy, or modified lithotomy position, and is anesthetized. A vertical midline perineal incision 110 (see FIG. 6) is formed between the scrotum and the anus. Tissue is dissected to expose the bulbous muscle around the urethra. A suitable tool is used to direct the arm 104 into and through the first obturator foramen OF, and this procedure is repeated on the contralateral side to place the arm 106 into and through the second obturator foramen OF.

One suitable approach of placing the arms 104, 106 through the obturator foramen OF is described as an "outside-in" approach. The outside-in approach includes directing a needle or other device through the skin of the groin area of the patient external of the obturator foramen OF along a curved path through the membrane M and around the ischial pubic ramus R such that the tool exits the midline perineal incision 110. One of the arms 104, 106 is attached to the tool, and the tool is withdrawn along its curved pathway back around the ischial pubic ramus IR, through the membrane M, out of the obturator foramen OF, and out of the skin at the groin area. In this manner, each arm 104, 106 is directed through and placed in one of the obturator foramen OF. The arms 104, 106 are trimmed to a subcutaneous level. A holding stitch is placed to hold the arm 104, 106 relative to the groin tissue, as determined by the surgeon.

A different approach is the "inside-out" approach in which the needle or tool is coupled to the support and directed from the perineal incision (inside) outward to the skin at the groin area (outside). Placement of the arms 104, 106 with the inside-out approach is also acceptable.

One acceptable single incision approach includes the formation of a single (exactly one) incision in the urogenital triangle. Tissue is dissected distal the incision to access the urethra and the pelvis. The arms 104, 106 of the support 100 are directed into the single incision and anchored to the membrane M of the obturator foramen OF, for example with the anchor 22 (FIG. 1). The pre-pubic portion 108 is inserted into the single incision and fixed to the periosteum tissue over the pubic bone PB by the anchor 22 as delivered by the introducer 24. In this manner, a treatment for urinary incontinence is provided to the patient by forming exactly and only one incision and implanting the support 100 through that single incision.

Figure 6:
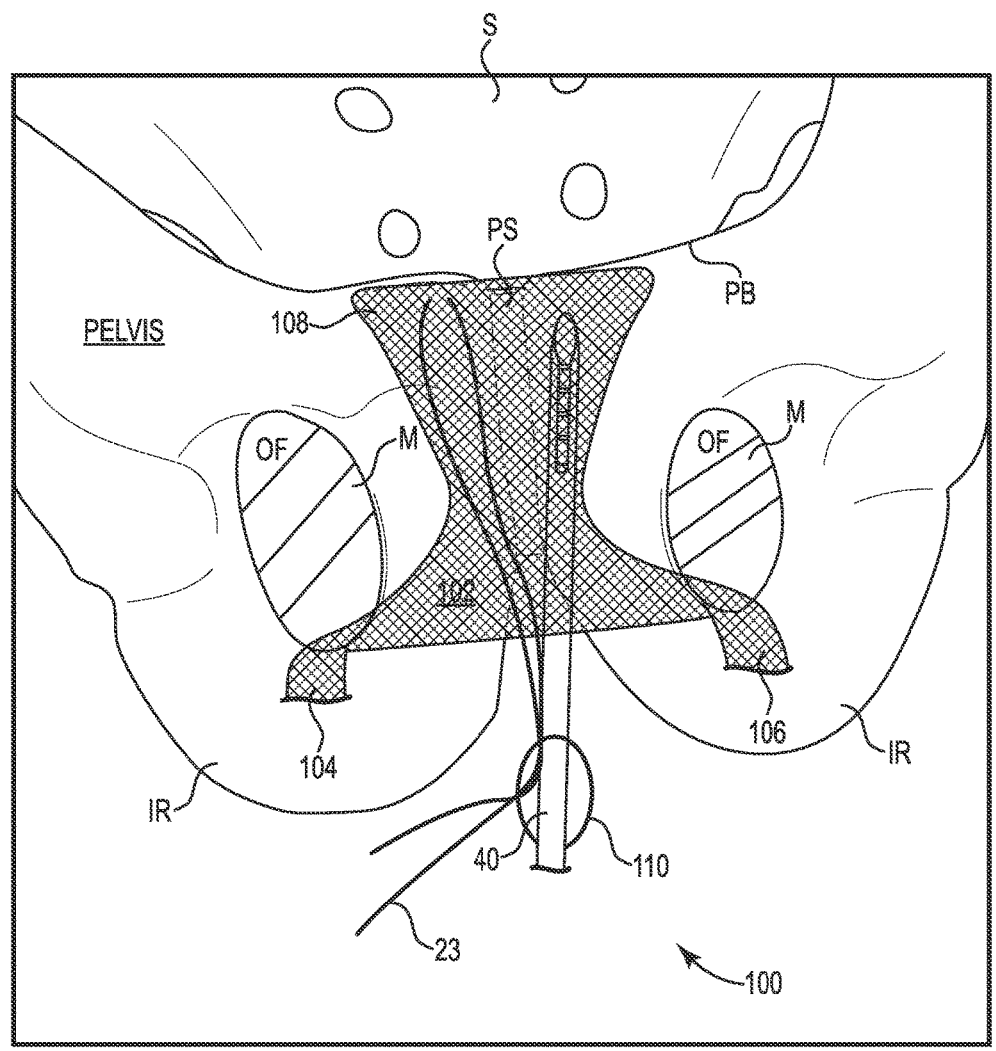
FIG. 6 is a schematic view of one embodiment of the surgical system employed to anchor a support material to the tissue of the human body showing a pre-pubic portion being attached to the periosteum of the pubic bone.

FIG. 6 is a schematic view of the surgical system 20 employed to fixate the pre-pubic portion 108 of the support 100 to the periosteum tissue of the pubic bone PB. The cannula 40 of the introducer 24 is inserted into the perineal incision 110 and directed to the pubic bone PB anterior to the pelvis.

In one suitable approach, the anchor 22 is driven through the material of the support 100 and into the periosteum tissue that covers the pubic bone PB. The cannula 40 pierces the periosteum tissue and slides along the bone of the pelvis without entering or penetrating the bone. The anchor 22 is engaged under the periosteum tissue and the suture 23 extends through the support 100 out through the perineal incision 110. The surgeon, depending upon surgeon preference, will place at least one anchor 22 through the pre-pubic portion 108 an each side of the pubic symphysis PS. The suture 23 extends from each anchor out through the perineal incision 110 and is available for subsequent tying or other termination.

In a different suitable approach, the anchor 22 is loaded into the introducer 24 and the cannula 40 is introduced in the perineal incision 110 up to the pubic bone PB anterior to the pelvis. The introducer 24 is employed to drive the anchor 22 under the periosteum tissue of the pubic bone PB and the cannula 40 is withdrawn through the perineal incision 110. The suture 23 trails behind the anchor 22 and exits the body at the incision 110. An end of the suture 23 is inserted through the pre-pubic portion 108 of the support 100, and the pre-pubic portion 108 is guided along the suture 23, through the incision 110, and up to the pubic bone PB. Thereafter, the suture 23 is tied or terminated to hold the pre-pubic portion 108 against the pubic bone.

Figure 7:
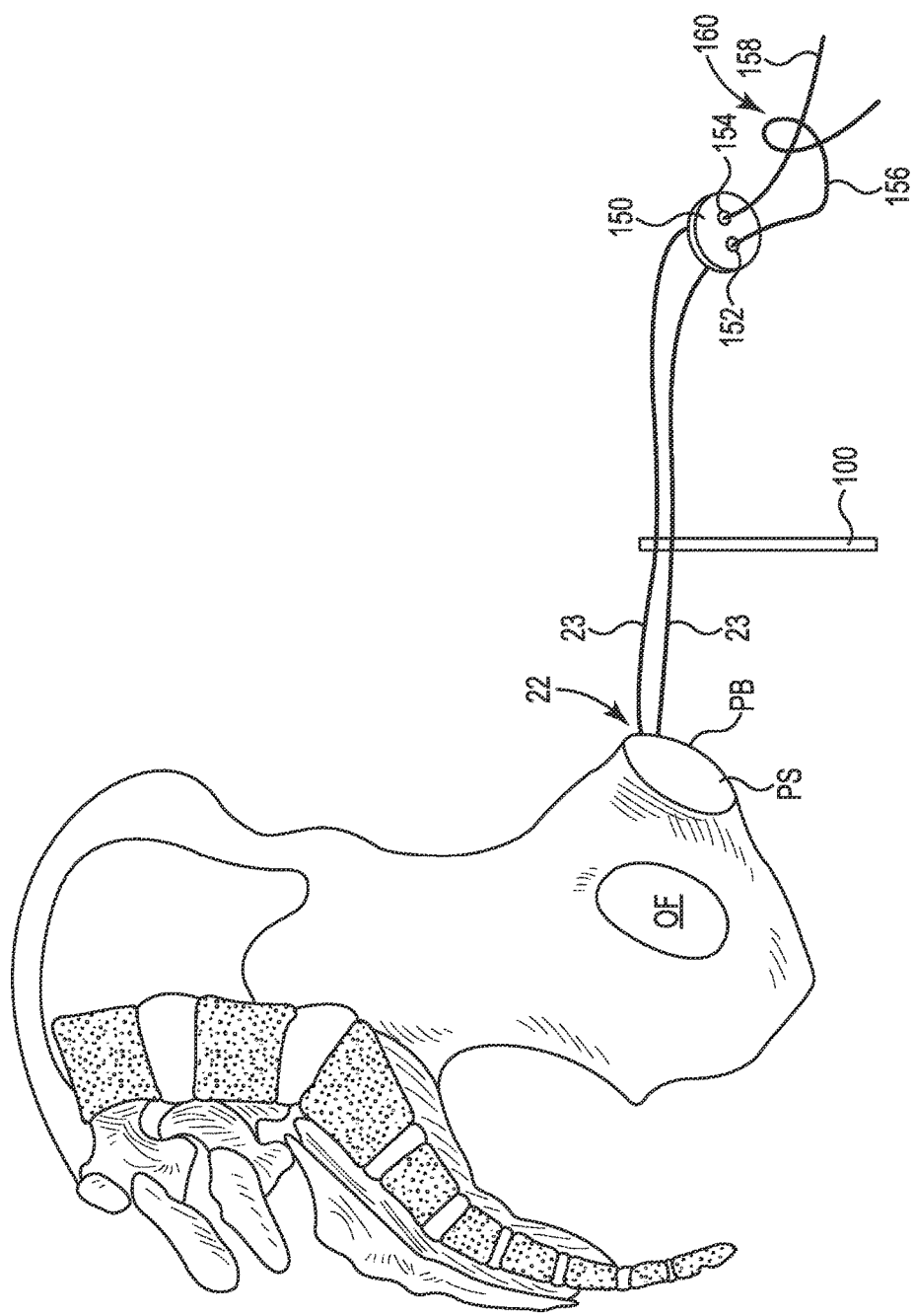
FIG. 7 is a schematic view of the anchor illustrated in FIG. 1 secured to tissue with a stopper coupled with a suture and located between the anchor and a slip knot.

FIG. 7 is a schematic view of the anchor 22 secured to the periosteum tissue and the support 100 secured to the suture 23. In one embodiment, the system 20 described above includes a stopper 150 that is attached to the suture 23, where the stopper 150 is configured to slide along the suture 23 and direct the support 100 into the patient's body and against the tissue. In one embodiment, the stopper 150 has a first orifice 152 and a second orifice 154. One or more of the anchors 22 is engaged with the periosteum tissue of the pubic bone PB, and a first end 156 of the suture 23 extends from the anchor 22 through the first orifice 152, and a second end 158 of the suture 23 extends to the second orifice 154. The stopper 150 slides along the suture 23 and is operable to push or otherwise deliver the support 100 against the pubic bone PB. In one embodiment, a slip knot 160 or other termination device is provided to tie the suture 23 against the stopper 150 after the stopper 150 and the support 100 has been delivered to the pubic bone PB. The stopper 150 is located between the anchor 22 and the slip knot 160.

Suitable materials for fabricating the stopper 150 include plastics or metal. One suitable material for fabricating the stopper 150 includes polypropylene. Another suitable material for fabricating the stopper 150 includes stainless steel. In one embodiment, the stopper 150 is fabricated to be bioabsorbable.

Figure 8:
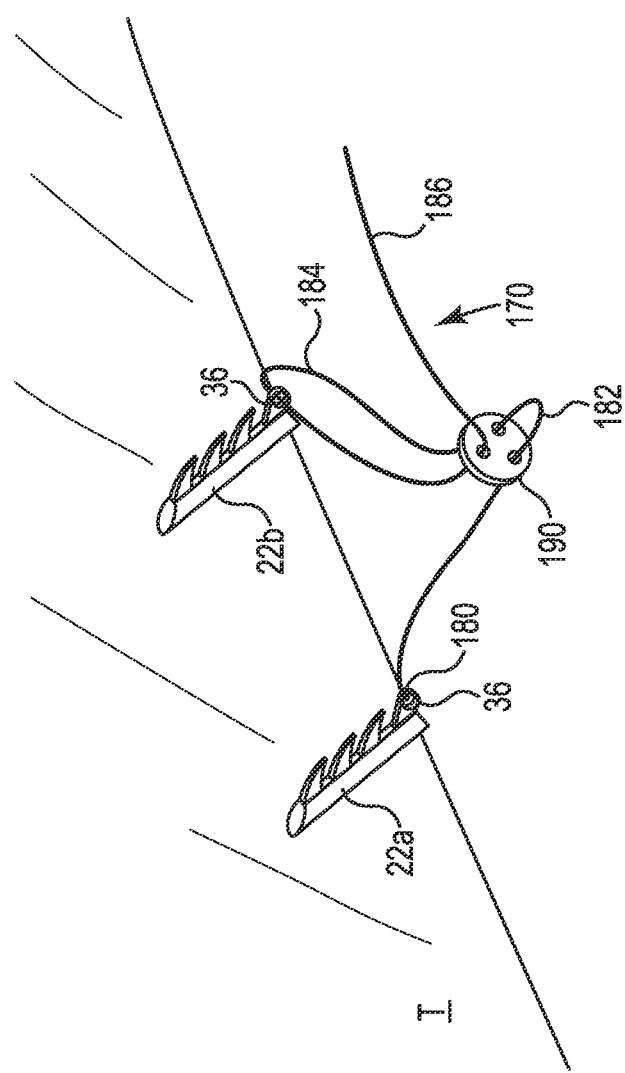
FIG. 8 is a schematic view of two anchors as illustrated in FIG. 1 secured to tissue and coupled with a suture.

FIG. 8 is a schematic view of two anchors 22 secured to tissue T and coupled with a suture 170. The anchors include a first anchor 22a and a second anchor 22b. The anchors 22 are engaged with the tissue T, for example through the use of the introducer 24 (FIG. 1). A suture 170 is provided having a first end 180 terminated to the eyelet 36 of the anchor 22a, a mid-portion 182 of the suture located between the first anchor 22a and the second anchor 22b, and a portion 184 of the suture in sliding engagement with the eyelet 36 of the second anchor 22b. A free end 186 of the suture 170 is provided, and pulling on the free end 186 of the suture 170 cinches the mid-portion 182 of the suture between the first anchor 22a and the second anchor 22b. In one embodiment, a slide knot 190 or sliding engagement feature 190 is coupled to the suture 170 and is so configured to secure or lock the mid-portion 182 of the suture in a desired position relative to the anchors 22. The slide knot 190 operates to cinch the suture 170 tightly against the support 100 (FIG. 6) against the tissue T.

Some male incontinence treatment devices have several arms, including some form of arms that traverse the obturator foramen and other arms that are implanted anterior to the pubic bone (called pre-pubic arms). The pre-pubic arms are tunneled anterior to the pelvis and exit the skin of the abdomen.

In contrast, embodiments of the system described above provide a support with two arms that are A) secured to the periosteum alongside the obturator foramen or B) secured to the membrane M covering the obturator foramen or C) secured through the obturator foramen and a system 20 to attach a portion of the support directly and efficiently to the periosteum tissue over the pubic bone. The system obviates the use of additional pre-pubic arms that are tunneled under and affixed to the skin. The system is easier to implant and reduces the amount of time that the patient is in the operating room.

FIGS. 9-17 are schematic views illustrating embodiments of a method of anchoring a support material to tissue.

Figure 9:
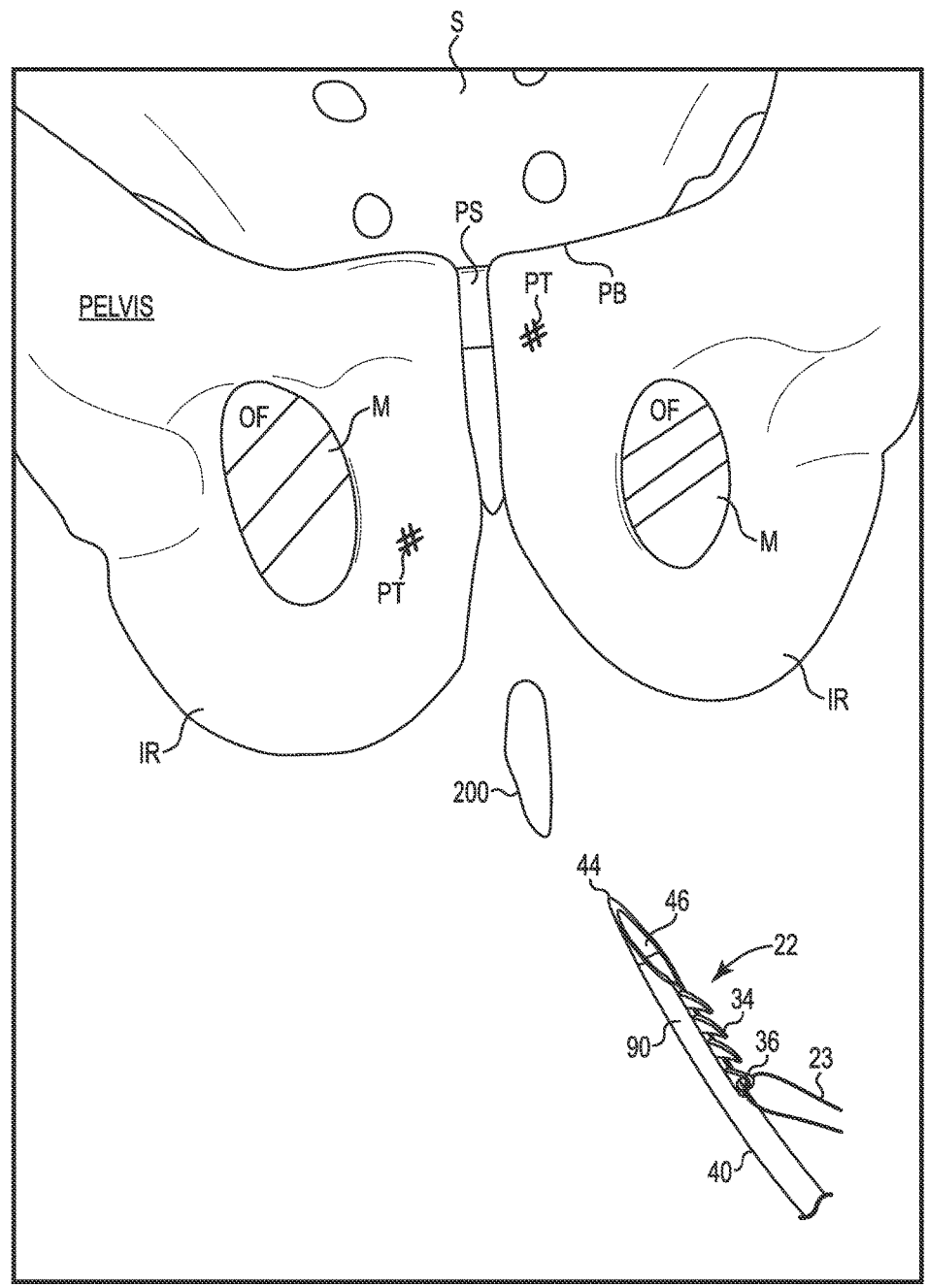
FIGS. 9-17 are schematic views of embodiments of a method of anchoring a support material to tissue.

FIG. 9 is a schematic view of a pelvis. The view has been simplified by not illustrating certain extraneous aspects of human anatomy such as certain of the organs and certain of the muscle and other connective tissues. The view is oriented from a location anterior to the pelvis and shows the sacrum S in the background and the pubic symphysis PS in the foreground.

The patient is prepared for surgery according to the accepted procedures of the hospital or clinic, suitably anesthetized, and placed in a lithotomy position with the feet elevated above the level of the hips and the perineum at the edge of the surgical table. An incision 200 is formed in the urogenital triangle of the patient. The urogenital triangle is that region on a female patient where a base leg of the urogenital triangle is oriented in a horizontal manner between the vagina and the anus, and the pair of generally equilateral legs of the urogenital triangle extending from the base leg meets at an apex above the vertex of the labia. The urogenital triangle is that region on a male patient between the scrotum and the anus. Tissue is dissected away from the incision 200 to access the urethra, and in some procedures, the ischial pubic rami IR.

The method of anchoring a support material to tissue includes first forming the incision 200 in the urogenital triangle of a male patient or a female patient for access to the pelvic anatomy. Thereafter, one of the anchors 22 is placed in the tissue (i.e., not in the bone) leaving the suture 23 trailing out of the incision. The support is delivered along the suture 23 in a distal direction (e.g., along an inward direction) to the location of the anchor 22. The suture 23 is terminated to the support to fixate the support inside the patient. Consistent with this description, the anchor 22 is inserted into the cannula 40 of the introducer 24. Specifically, the body portion 30 (FIG. 2A) of the anchor 22 is inserted into the lumen 46 such that the spine 34 extends radially out of the wall 90 of the cannula 40. In one embodiment, the eyelet 36 extends radially out of the wall 90 of the cannula 40 to provide both a pushing/driving surface for the cannula 40 and a tissue engagement surface. The introducer 24 is now readied to affix the anchor 22 to the tissue.

Figure 10:
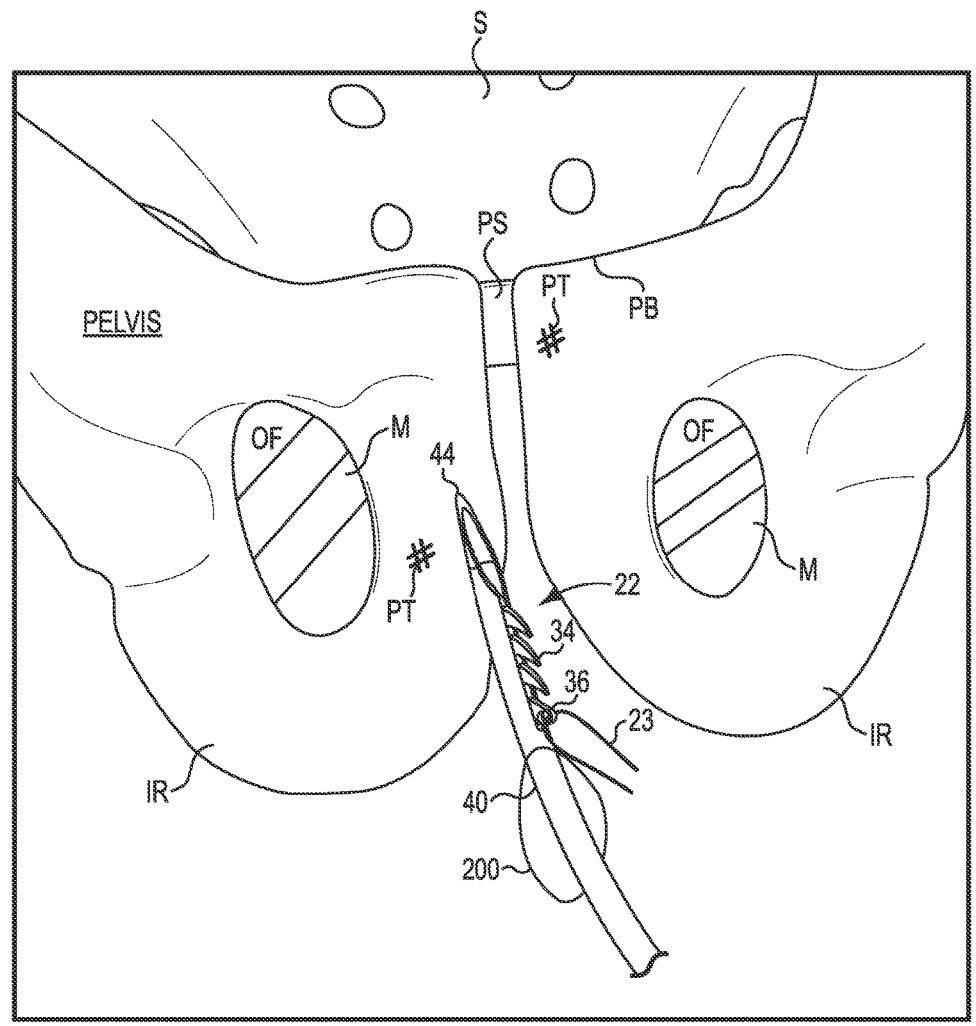

FIG. 10 is a schematic view of the leading end 44 of the cannula 40 inserted into and guided through the incision 200. The surgeon palpates for the surface of the pelvis and thereafter pushes the leading end 44 of the cannula 40 into the periosteum tissue PT of the pelvis until the spine portion 34 of the anchor 22 is engaged with (e.g., under) the periosteum tissue PT. Periosteum tissue is a thin sheet of dense fibrous connective tissue that is attached at the outer surface of all bones. The periosteum tissue PT is represented as a hashed area and it is understood that the periosteum tissue PT covers the exterior of the boney pelvis.

Figure 11:
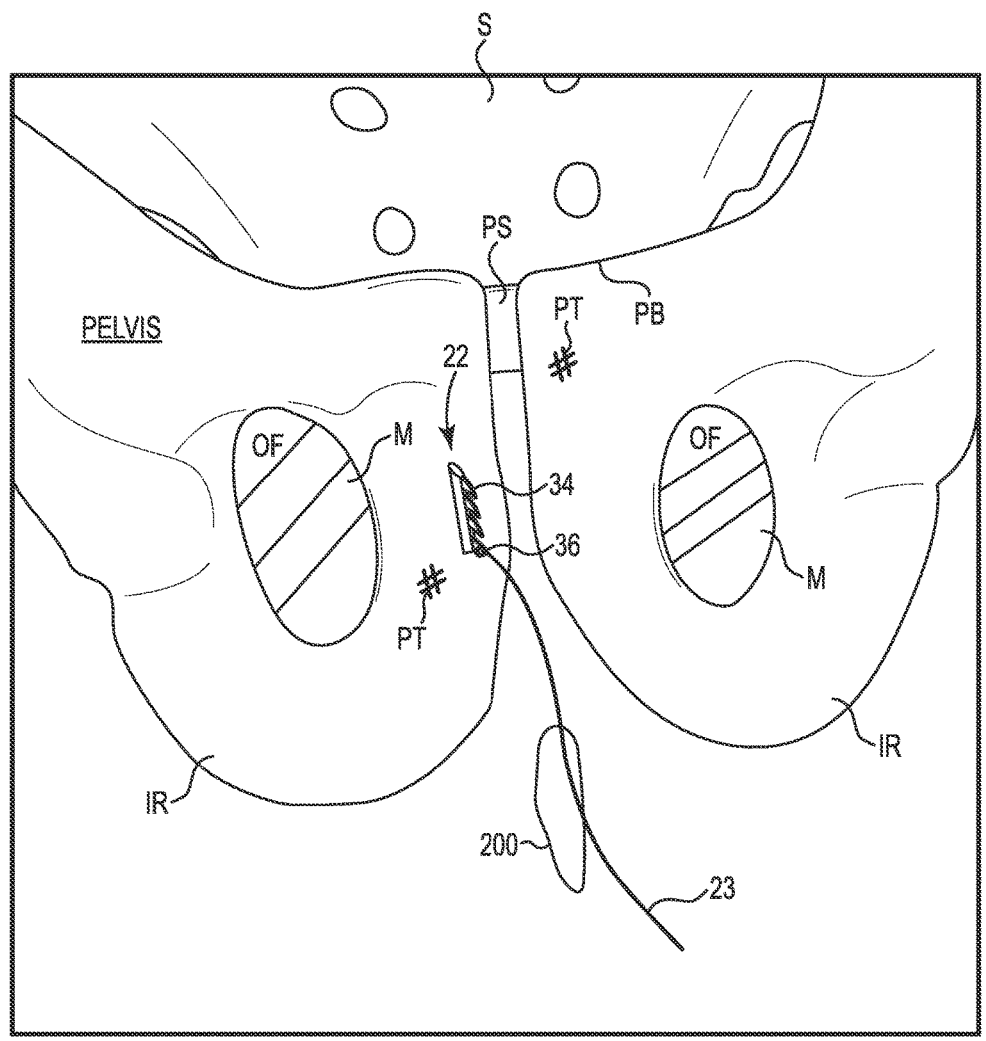

FIG. 11 is a schematic view of the anchor 22 engaged with the periosteum tissue PT. The cannula 40 (FIG. 10) has been withdrawn from an incision 200 leaving the anchor 22 embedded or engaged with the periosteum tissue PT. The anchor 22 is under the periosteum tissue PT and over (or above or superior) to the bone of the pelvis. The anchor 22 is not inserted into the bone of the pelvis. The suture 23 is connected to the anchor 22, and a portion of the suture 23 extends out of the incision 200 and is available (for example as a conduit) to allow the surgeon to deliver support material along the suture 23 to the anchor 22. In this manner, since the anchor 22 is embedded in the periosteum tissue PT a support can be delivered to the anchor and fixed against nearly any bone in the body. Thus, the surgeon need not "aim" for the obturator foramen or other specific tissue landmark; the surgeon simply anchors the anchor 22 into periosteum tissue PT.

Figure 12:
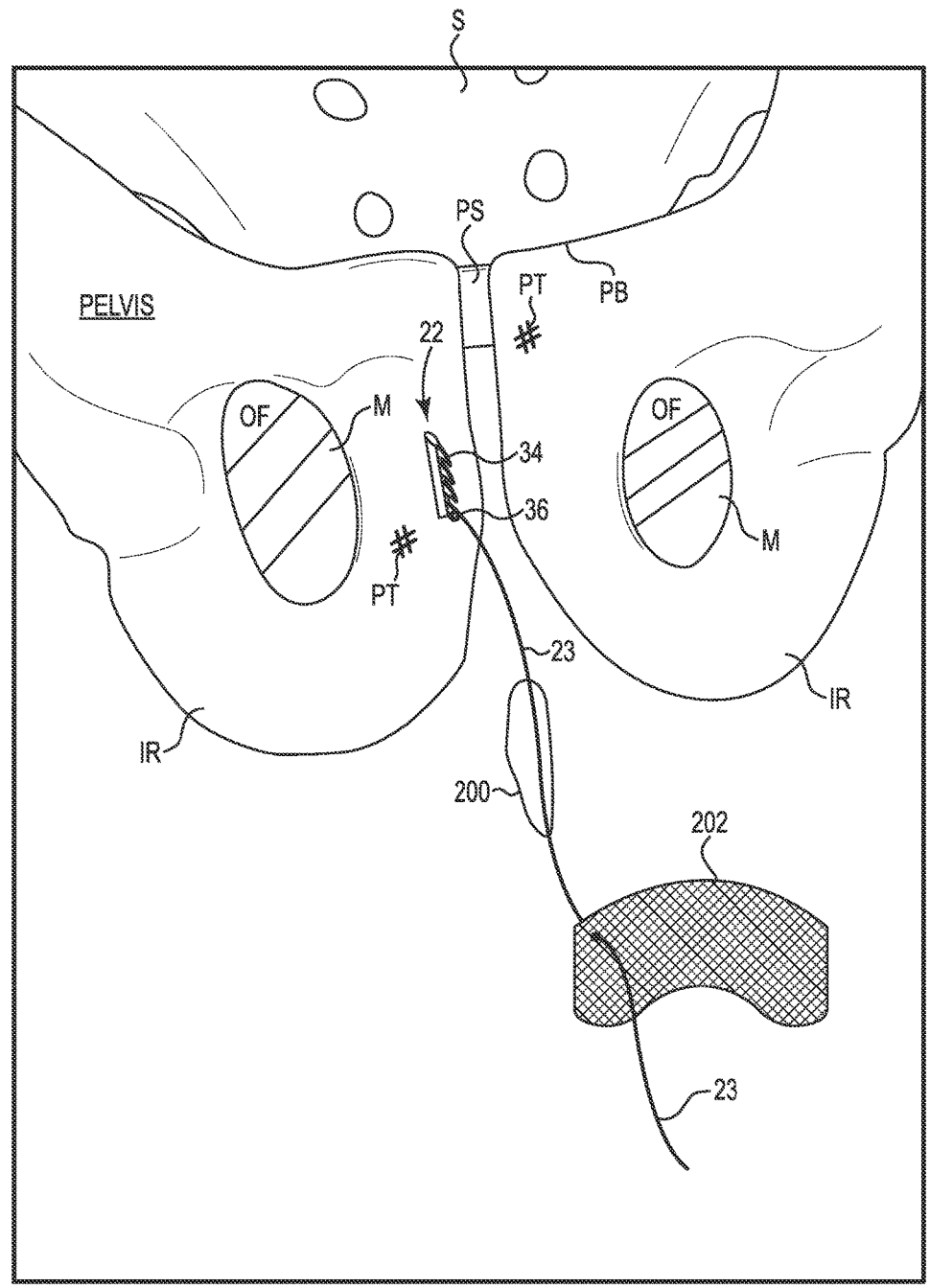

FIG. 12 is a schematic view of support material 202 coupled in sliding engagement with the suture 23. The support material 202 is illustrated in a generalized form. The support material 202 includes an area of a support. In some embodiments, one or more arms or one or more legs extend from the area of support material 202. In some embodiments, the support material 202 is just an area of material without arms or legs, for example a trapezoid or a rectangle of material that allows the surgeon to trim a desired shape (i.e., a "trim-to-size" support). The support material 202 is acceptably fabricated from the material of the support 100 described above.

The surgeon secures the support material 202 to the suture 23, for example by guiding the suture 23 through a pore or other opening of the support material 202. If the support material is a solid and does not have an opening, the surgeon employs a needle to direct the suture 23 through the support material 202. The portion of the suture 23 that extends out incision 200 allows the surgeon to conveniently couple the support material 202 to the suture 23 outside of the patient's body.

Figure 13:
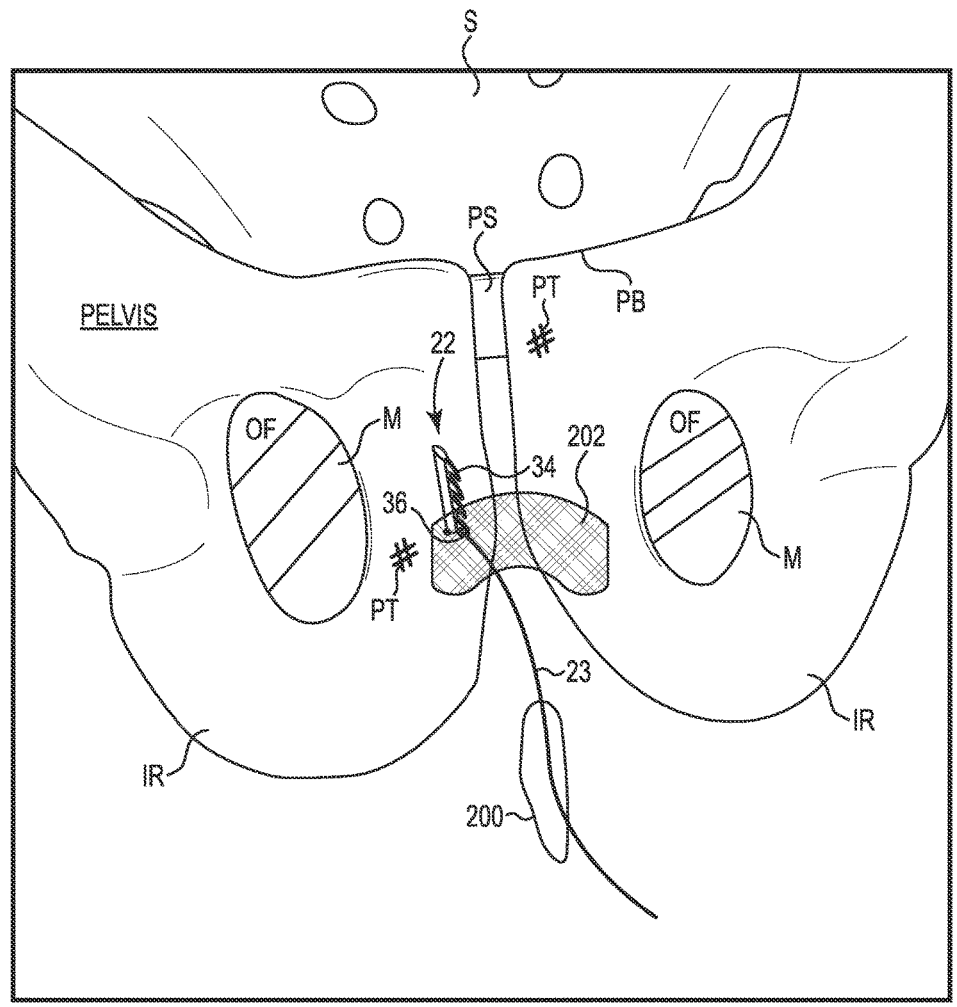

FIG. 13 is a schematic view of the support material 202 having been delivered along the suture 23, through the incision 200, in a distal direction to the patient's pelvis. The surgeon uses an instrument, or perhaps a finger, to guide the support material 202 through the incision 200 inward toward the pelvis. The anchor 22 is buried or otherwise implanted into the periosteum tissue PT, and the support material 202 is proximal to the anchor 22.

Figure 14A:
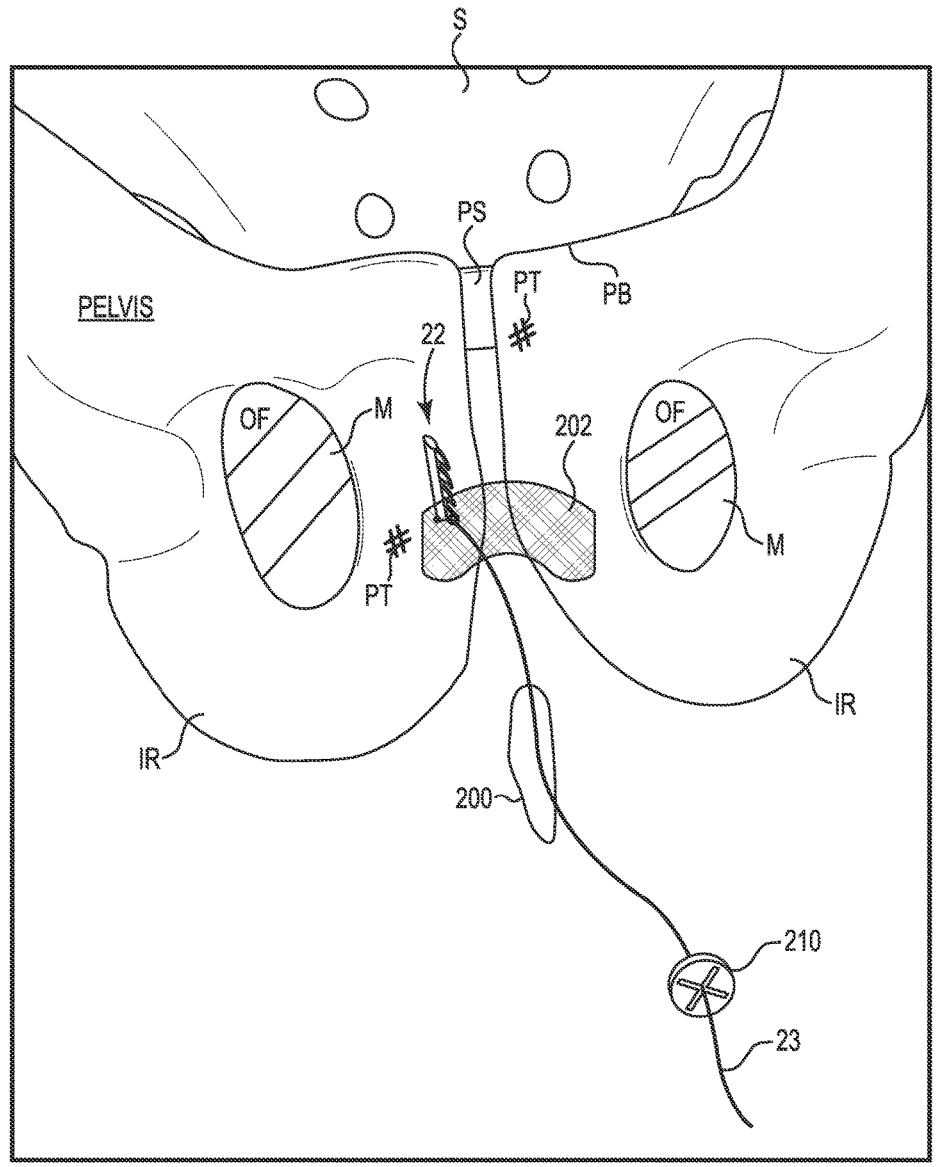

FIG. 14A is a schematic view of the support material 202 located between the anchor 22 and a stopper 210. The support material 202 has been delivered through the incision 200 to the pelvis of the patient, and the stopper 210 is configured to engage with the suture 23 and fixate the support material 202 against the pelvis. The anchoring of the support material 202 to the pelvis will support the urethra of the patient. The stopper 210 is configured such that sliding the stopper 210 along the suture 23 will forcibly affix the support material 202 to the patient. In one embodiment, the stopper 210 is configured for one-directional sliding along anchor 23, for example, only in a direction into the patient. The stopper 210 includes fingers that prevent the stopper 210 from moving in the direction out of the patient's body.

Figure 14B:
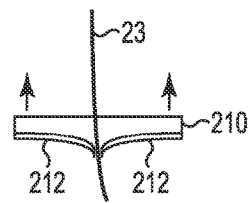

FIG. 14B is a schematic side view of the stopper 210 and the fingers 212. The fingers 212 are deflected to diverge away from the patient's body, which allows the stopper 210 to move along the suture 23 in the direction into the patient's body as indicated by the arrows. The stopper 210 is configured as a unidirectional stopper that is allowed to move in one direction along the suture 23. Attempted movement of the stopper 210 in the opposite direction causes the fingers 212 to impinge against the suture 23, which prevents movement of the stopper 210 of the patient's body.

Figure 15:
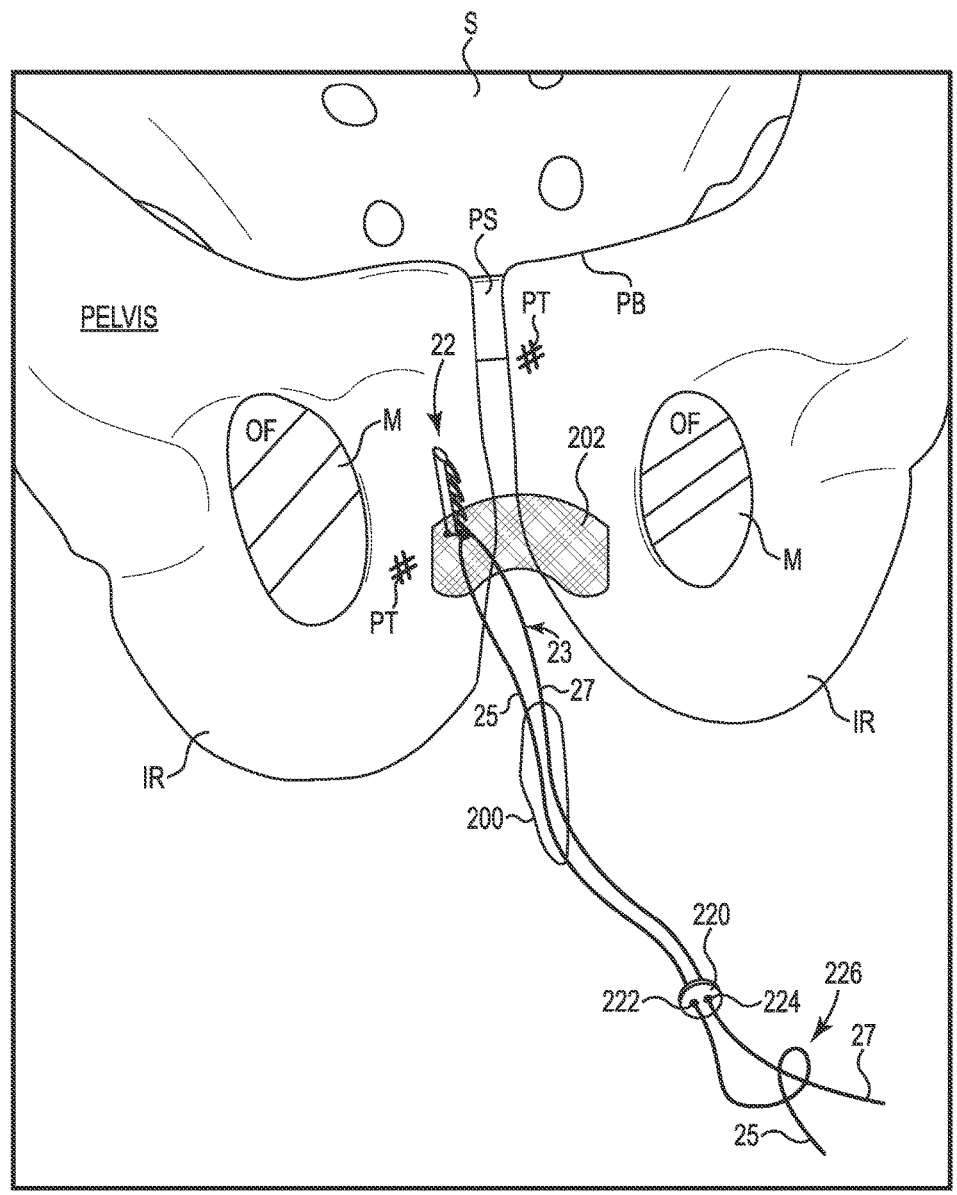

FIG. 15 is a schematic view of one embodiment of a stopper 220 provided to secure the support material 202 within the patient. The stopper 220, also referred to as a button 220, includes a first orifice 222 and a second orifice 224. The suture 23 includes a first strand 25 that is inserted through the first orifice 222 and a second strand 27 that is inserted through the second orifice 224. The button 220 is operable to slide along the suture 23 as the strands 25, 27 slide through the orifices 222, 224, respectively. In this manner, the button 220 is operable to be delivered through the incision 200 and into the patient. It is desirable to secure the button 220 against the support material 202. In one embodiment, the first strand 25 is tied to the second strand 27 to provide a slip knot 226. Pulling on the free end (e.g., strand 25) drives the slip knot 226 in a distal direction into the patient until the slip knot is secure against the button 220. Eventually, that portion of the suture 23 that is proximal of the button 220 is tied or otherwise terminated, and the excess suture 23 is removed by the surgeon.

Figure 16:
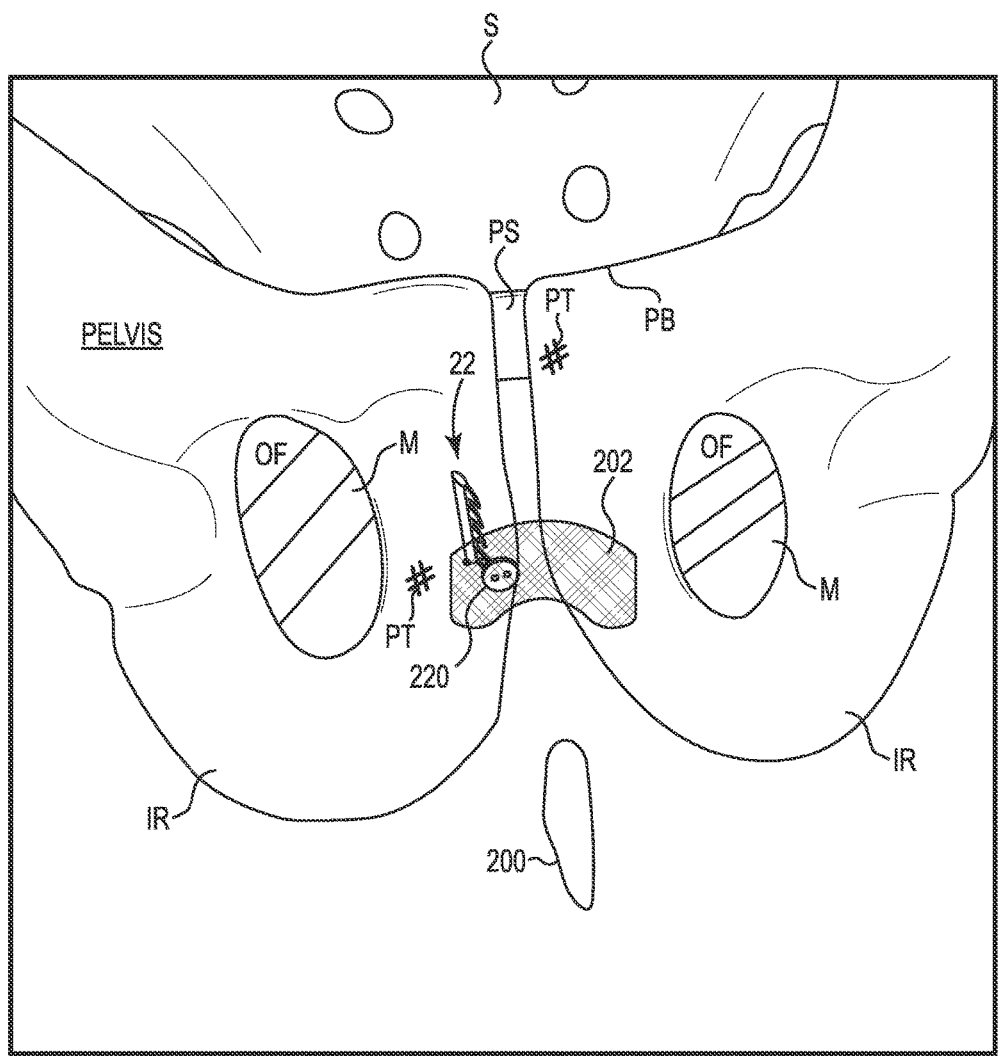

FIG. 16 is a schematic view of the support material 202 secured to the patient and located between anchor 22 and the stopper 220 (or button 220). The excess portion of the suture 23 has been removed. Other portions of the support material 202 may also be secured to other tissue of the patient, for example in a bilateral manner by using the introducer 24 and the anchor 22 as described above.

Figure 17:
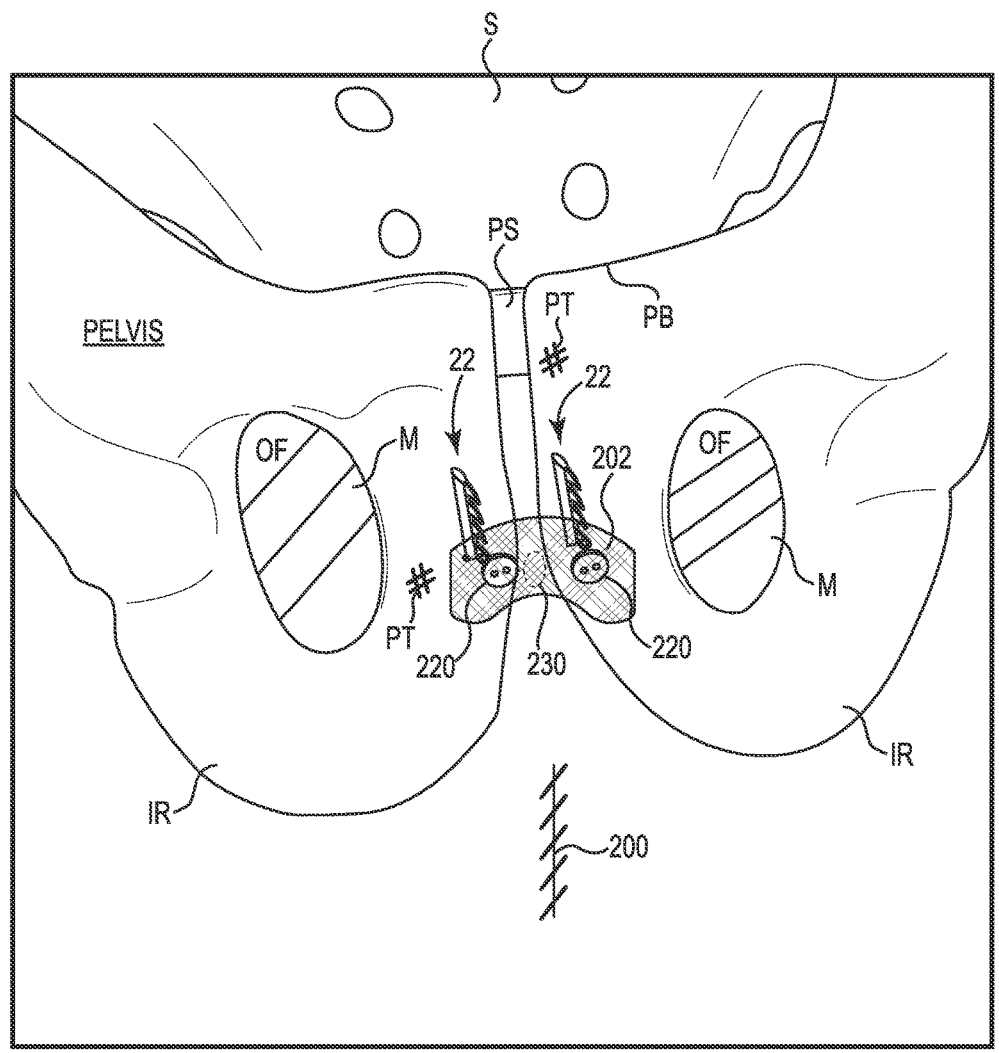

FIG. 17 is a schematic view of the support material 202 secured to the periosteum tissue PT of the patient on either lateral side of the pubic symphysis PS. The support material 202 is secured or fixated at two locations, a left side location (relative to the view of FIG. 17) and a right location. Each fixation location has the support material 202 positioned between the anchor 22 lodged in the periosteum tissue and the stopper 220, with the excess portion of the suture 23 removed. When the surgeon is satisfied that the support material 202 is appropriately placed and fixated, the incision 200 is closed.

In the case of a male patient, the support material 202 has a trapezoidal shape that is sized to support the bulbar urethral complex 230 (muscle and other tissue) and elevate and support the male urethra. The support material 202 in the case of the male patient is typically secured in more than two bilateral locations to allow substantial support and elevation to the longer male urethra.

In the case of a female patient, the support material 202 has a rectangular (e.g., "sling") shape of about 1 cm wide by 5-10 cm long that is sized to extend across the descending rami to support the short (~2 cm) female urethra 230. The support material 202 in the case of the female patient is typically secured in two bilateral locations to provide support without compression (or with reduced compression to the urethra).

FIGS. 18-23 are schematic views illustrating embodiments of a method of anchoring a support 310 to tissue. The support 310 is a rectangular sling-style of support as is appropriate for treating female urinary incontinence.

Figure 18:
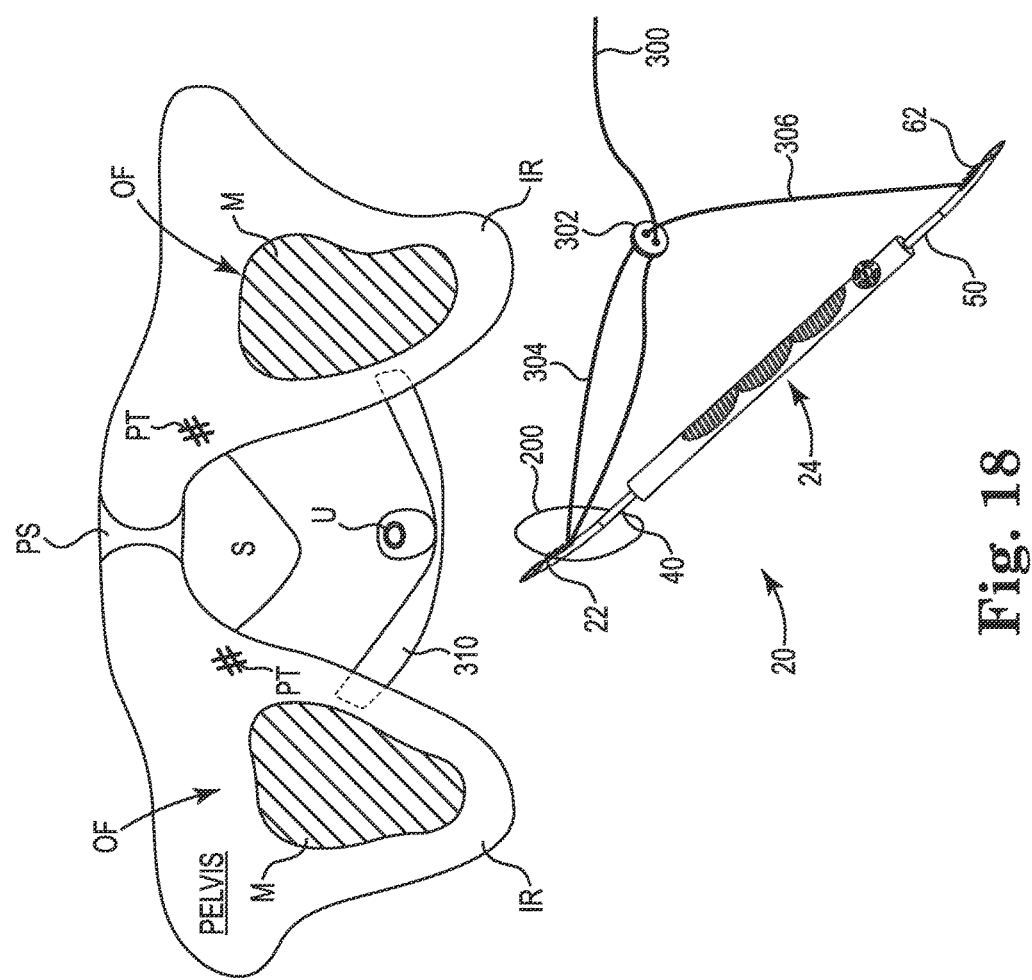
FIGS. 18-23 are schematic views of embodiments of a method of anchoring a support material to tissue.

FIG. 18 is a schematic view of the system 20 employed to secure the support 310 to the pelvis. The system 20 includes the first anchor 22 inserted into the first cannula 40, the second anchor 62 inserted into the second cannula 50, and a length of suture 300 connected between the first anchor 22 and the second anchor 62. The suture 300 is provided to slide relative to the first anchor 22 and includes a stopper 302 that fixes the suture 300 in a position selected by the surgeon.

Aspects of the surgical procedure include forming an incision 200 in a urogenital triangle, for example in the upper wall of the vagina and dissecting tissue to identify each of the two descending ischial pubic rami IR. The support 310 is inserted in the incision 200 after suitable dissection of the tissue. The system 20 is employed to anchor or fixate the support 310 in a position inferior to (under) the urethra U.

The anchor 22 is loaded into the first cannula 40 and the cannula 40 is introduced into the incision 200.

Figure 19:
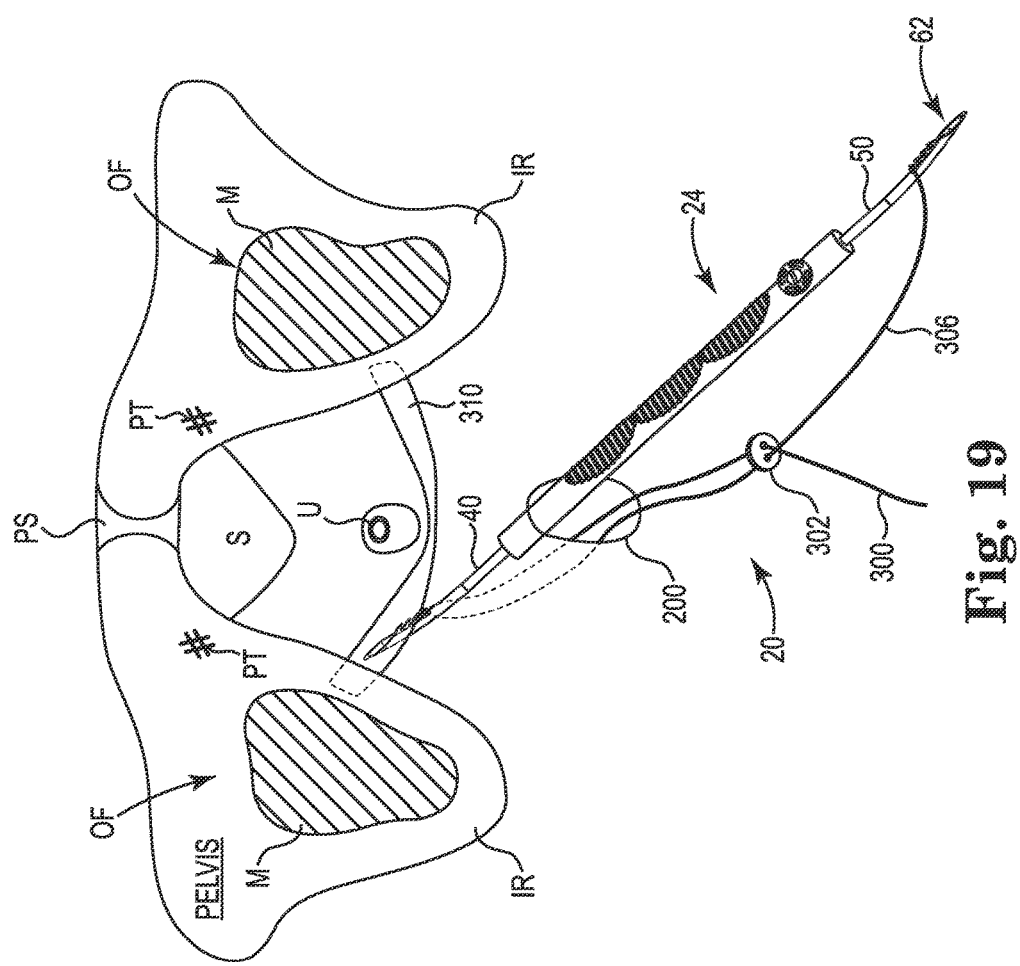

FIG. 19 is a schematic view of the support 310 relative to the pelvis and illustrates the first cannula 40 inserted through the incision 200, posterior the ramus IR, and through the support 300 until the leading end of the cannula 40 slides under the periosteum tissue PT. The leading end of the cannula 40 is sharp and so configured to pierce the periosteum tissue PT and deliver the anchor 22 between the bone and under the periosteum tissue PT.

Figure 20:
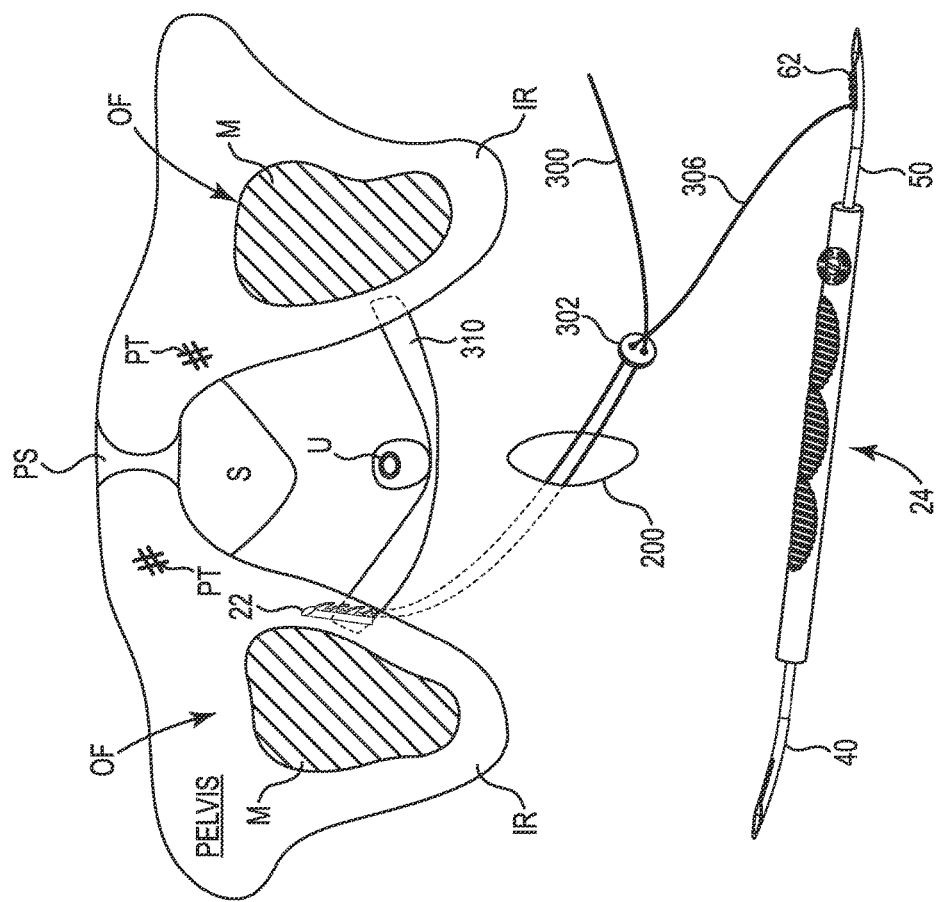

FIG. 20 is a schematic view of the first cannula 40 withdrawn from the incision 200 leaving the first anchor 22 embedded in or secured to the periosteum tissue PT. The suture 300 trails away from the first anchor 22 out of the patient through the incision 200.

Figure 21:
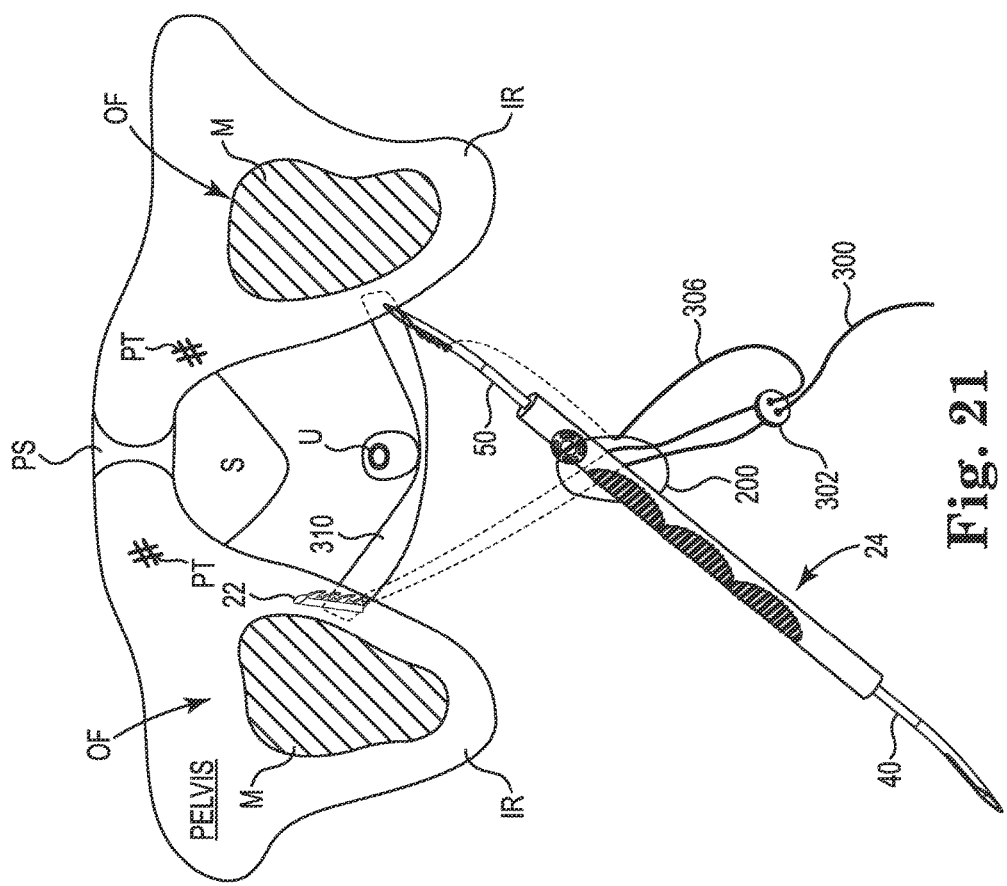

FIG. 21 is a schematic view of the second cannula 50 inserted into the incision 200, posterior to the ramus IR, and through the support 310. The surgeon directs the introducer 24 in a distal direction until the sharp distal end of the cannula 50 pierces the periosteum tissue PT and delivers the anchor 62. The suture 300 remains connected between the first anchor 22 and the second anchor 62, and the stopper 302 is outside of the patient's body.

Figure 22:
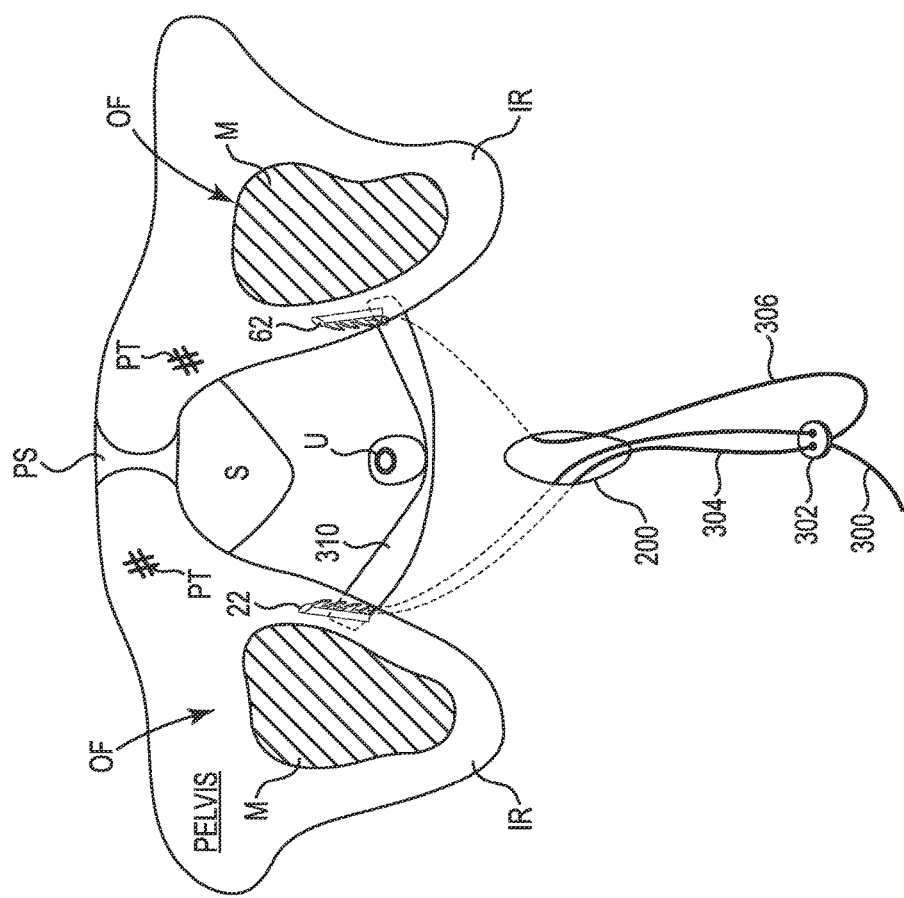
Figure 23:
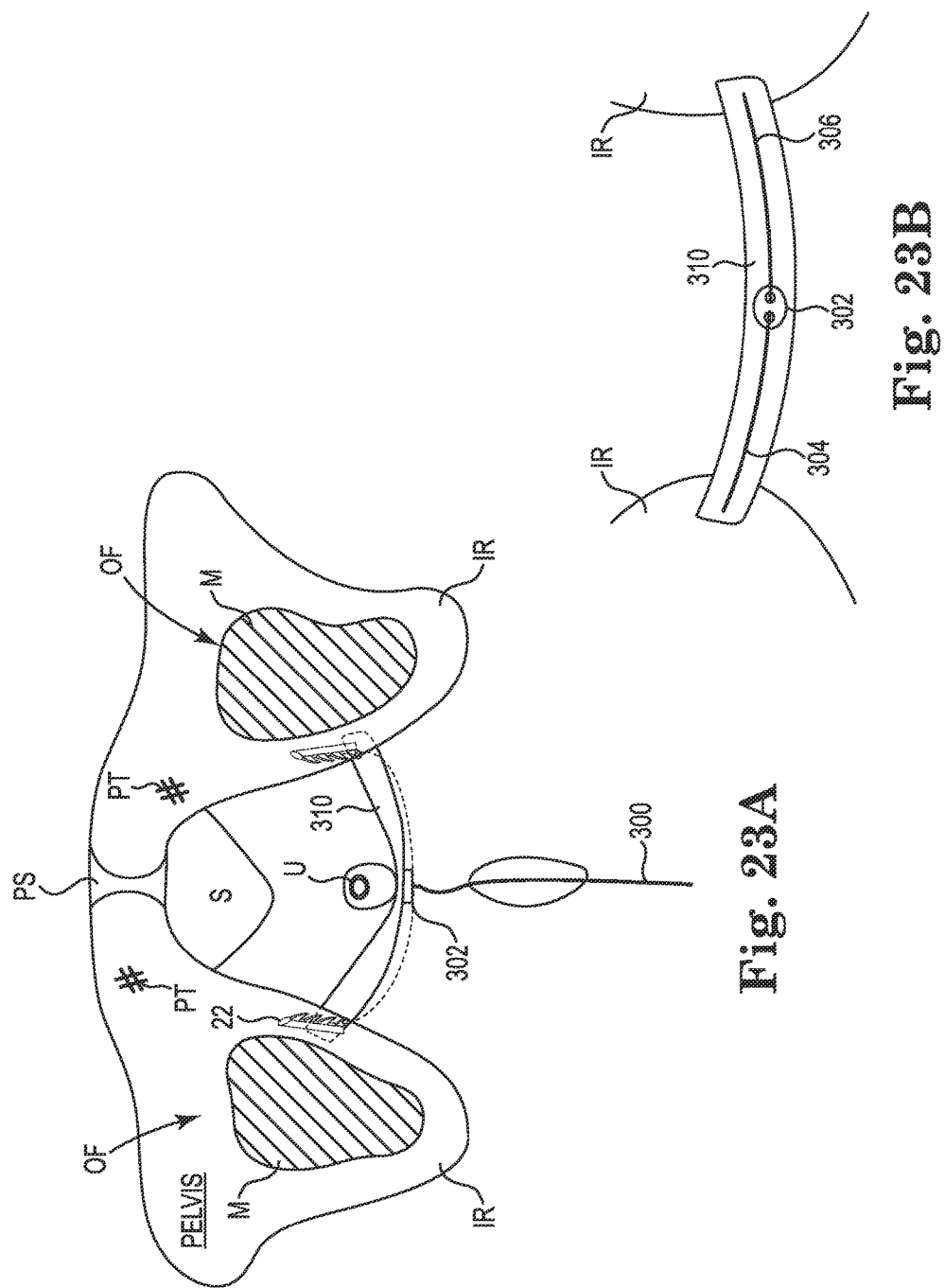

FIG. 22 is a schematic view of the support 310 secured on a first side by the first anchor 22 and secured on an opposite second side by the second anchor 62. The suture 300 is looped through the first anchor 22 and includes a first segment 304 between the anchor 22 and the stopper 302, a second segment 306 between the stopper 302 and the anchor 62, and the trailing portion 300. Pulling on the trailing portion 300 operates to cinch the stopper 302 into a supporting configuration against the support 310.

FIG. 23A is a schematic view of the support 310 secured relative to the pelvis, and FIG. 23B is a bottom view of the support 310 as secured between the opposed descending rami IR. The trailing portion 300 of the suture has been pulled by the surgeon in a proximal direction resulting in the stopper 302 being guided up to the support 310. The stopper 302 is configured to engage with the suture 300 and maintain the support 310 in position relative to the urethra U.

FIG. 23B illustrates the first segment 304 of the suture with the slack removed and tightened against the support 310, and the second segment 306 of the suture with the slack removed and tightened against the support 310. The stopper 302 secures the segments 304, 306 against the support 310.

Embodiments described above include pushing the pointed leading end of the cannula 40 through both the support 310 and the periosteum tissue PT to secure the anchor 22 in the patient. The trailing suture 300 is accessible by the surgeon outside of the patient's body to allow the surgeon to direct the stopper 302 upwards (or inwards) to the support 310.

In an alternative embodiment of this approach, the surgeon pushes the leading end of the cannula 40 into the periosteum tissue PT of the first ramus IR and engages the spine portion 34 of the first anchor 22 in the periosteum tissue, while leaving a single strand of suture 300 trailing from the first anchor 22 and out of the vaginal incision 200. The surgeon completes a similar process on the contralateral side by pushing the leading end of the cannula 40 into periosteum tissue PT of the second ramus IR and engaging a second, different anchor 22 with the periosteum tissue PT. A second, separate suture strand is left trailing from the second anchor and out of the vaginal incision 200. Along these two trailing suture strands the surgeon delivers a first end portion of a sling 310 along the first suture strand, through the vaginal incision 200 and to the first ramus IR of the pelvis, and a second end portion of the sling 310 along the second suture and through the vaginal incision 200 to the second ramus IR of the pelvis. The surgeon subsequently secures each suture strand, for example by tying the strand to form a knot at the sling 310.

Embodiments described above include pushing the pointed leading end of the cannula 40 through both the support 310 and the periosteum tissue. The trailing suture 300 is accessible by the surgeon outside of the patient to allow the surgeon to direct the stopper 302 upwards (or inwards) to the support 310. In an alternative embodiment of this approach, the surgeon fixates a support material 310 between opposed membranes M of the opposed obturator foramen OF. In such a procedure, the surgeon guides the leading end of the cannula 40 through a first end portion of the sling 310, through the vaginal incision 200, and into the membrane M of the first obturator foramen OF to engage the first anchor with the membrane M, thus leaving a suture connected to the first anchor. The surgeon performs a similar procedure on the contralateral side by loading another anchor into the cannula 40 and guiding the leading end of the cannula 40 through a second end portion of the sling 310, through the vaginal incision 200, and into a membrane M of a second obturator foramen OF. The surgeon engages the second anchor with the membrane M, where the suture is coupled to the second anchor. The surgeon pulls on a free end of the suture and secures the first end portion of the sling 310 to the first membrane M of the first obturator foramen OF and secures the second end portion of the sling 310 to the membrane M of the second obturator foramen OF.

FIGS. 24-28 are schematic views of embodiments of a method of anchoring a support to tissue.

Figure 24:
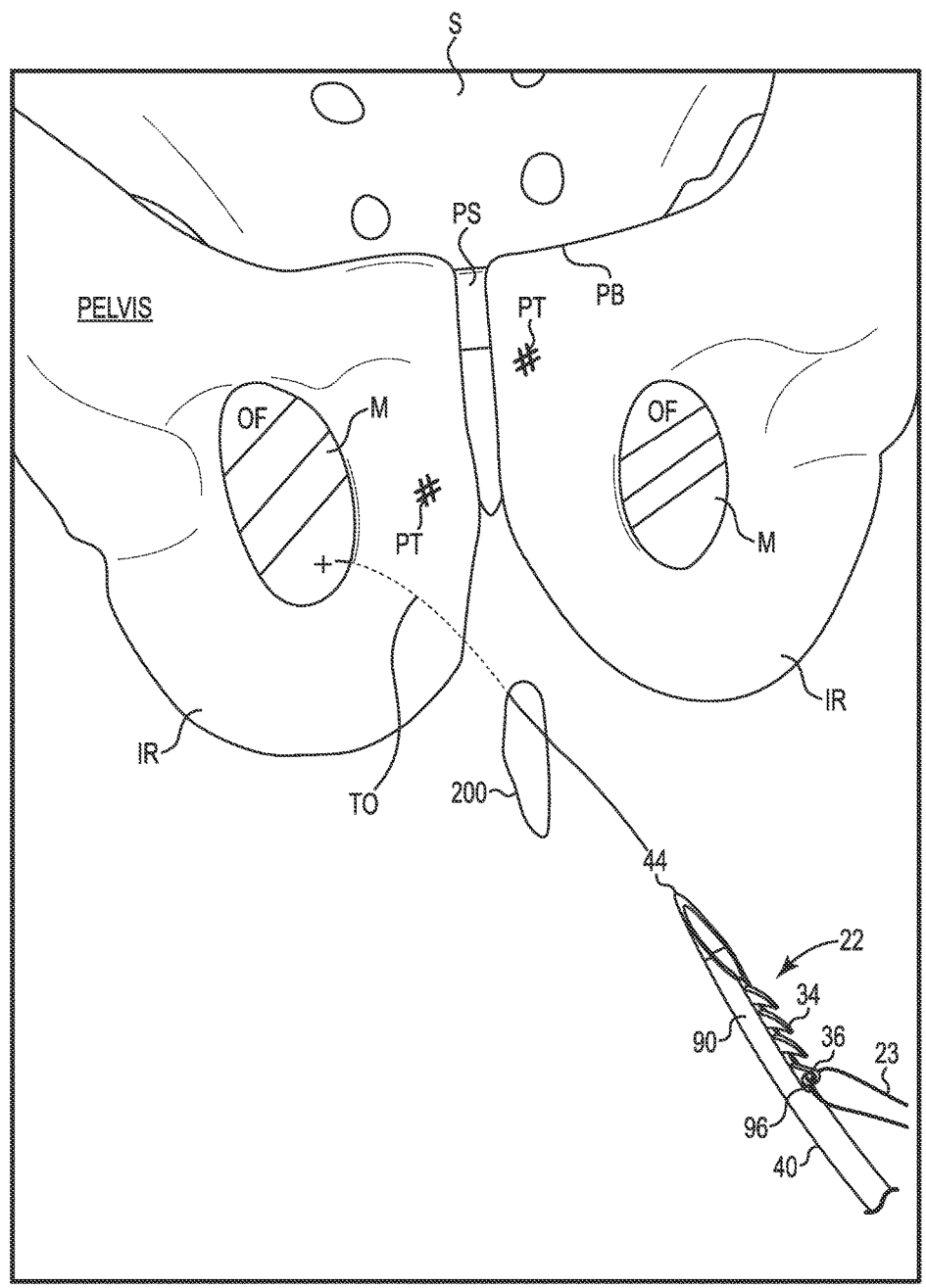
FIGS. 24-28 are schematic views of embodiments of a method of anchoring a support material to tissue.

FIG. 24 is a schematic view of a trans-obturator TO path that is followed by the cannula 40 to place the anchor 22 into the membrane M of the obturator foramen OF. The trans-obturator TO path extends from the incision 200 posterior to the ramus (i.e., behind the ramus) and into the membrane M. It is desirable to place the anchor 22 in a lower quadrant of the membrane M. In one approach, the surgeon palpates along the inferior portion of the ramus IR and guides the cannula 40 along and behind the ramus IR into the membrane M.

Figure 25:
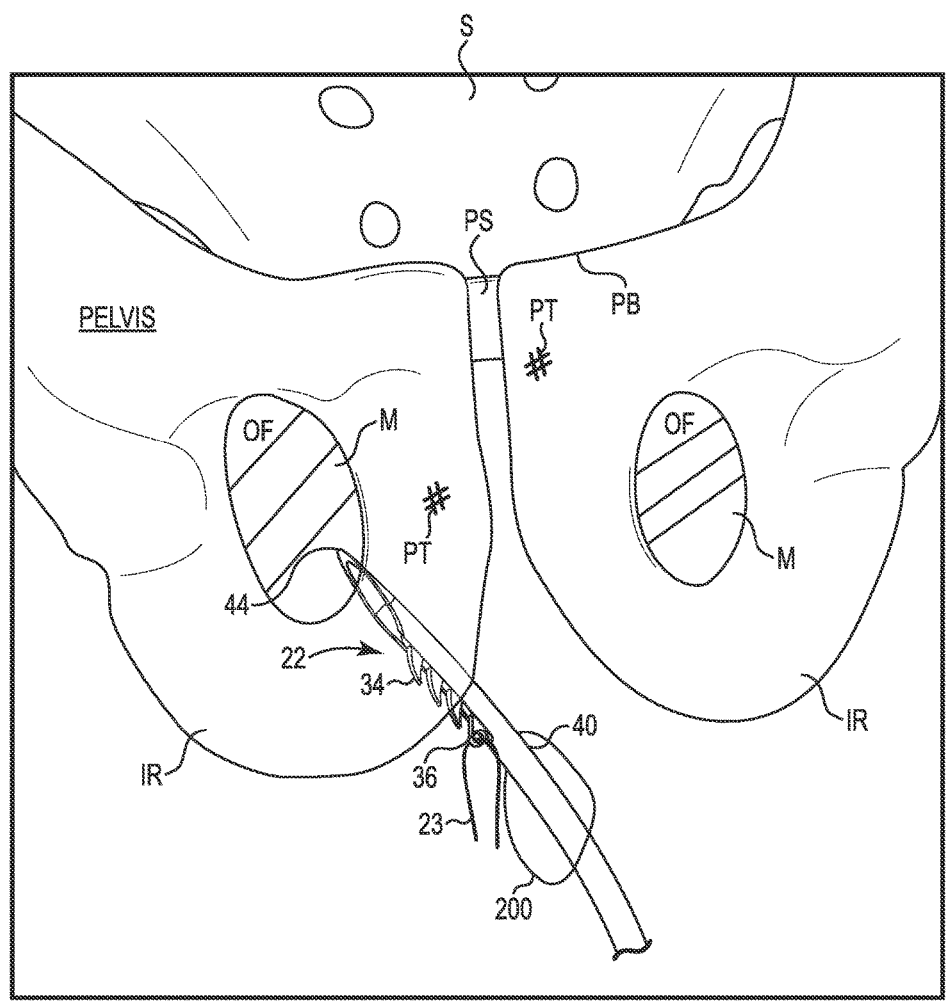

FIG. 25 is a schematic view of the cannula 40 introduced along the trans-obturator TO path posterior to the ramus IR and into the membrane M. The surgeon provides a pushing distal force that drives the anchor 22 into, but not through, the membrane M. It is not necessary to drive the anchor 22 all the way through the membrane M from the posterior side to the anterior side. However, in one embodiment the anchor 22 is inserted entirely through the obturator foramen OF from the posterior side to the anterior side of the membrane M.

Figure 26:
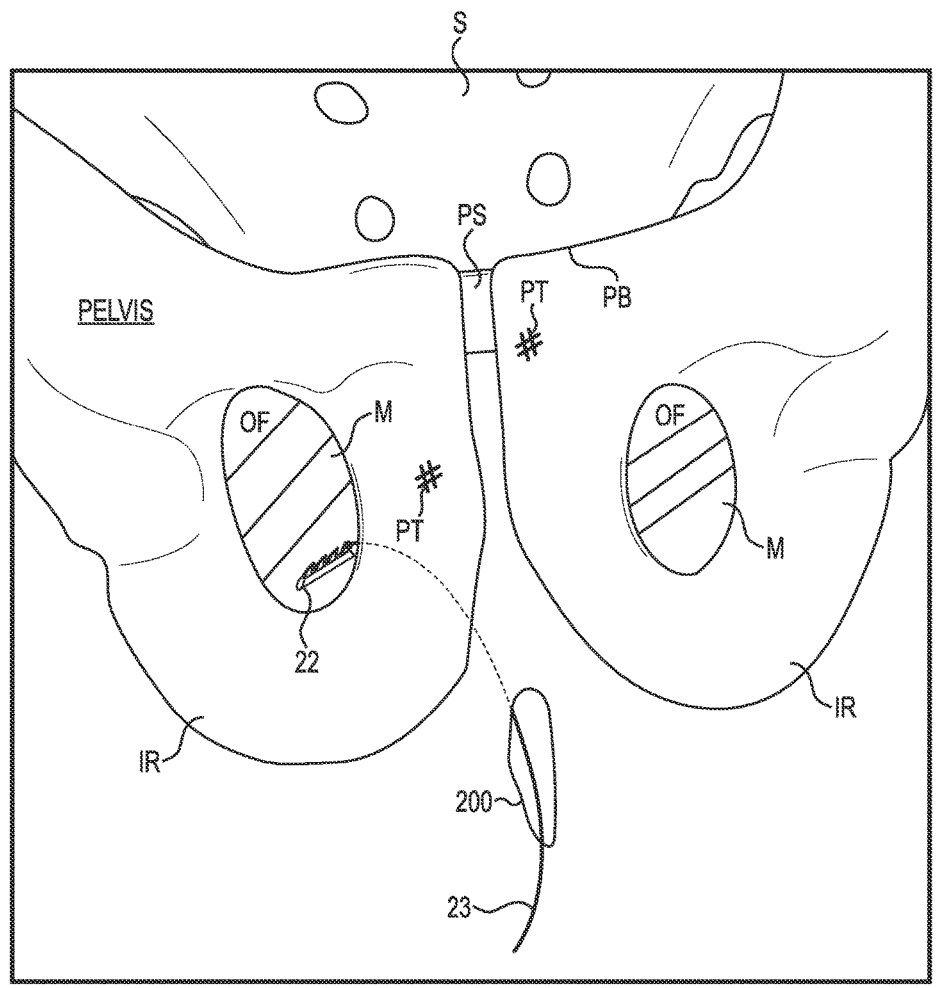

FIG. 26 is a schematic view of the anchor 22 inserted into the membrane M with the suture 23 extending posterior to the ramus IR and out of the incision 200. In this configuration, the suture 23 is available to deliver support material or other materials along the trans-obturator TO path posterior to the ramus IR upwards to the membrane M that covers the obturator foramen OF.

Figure 27:
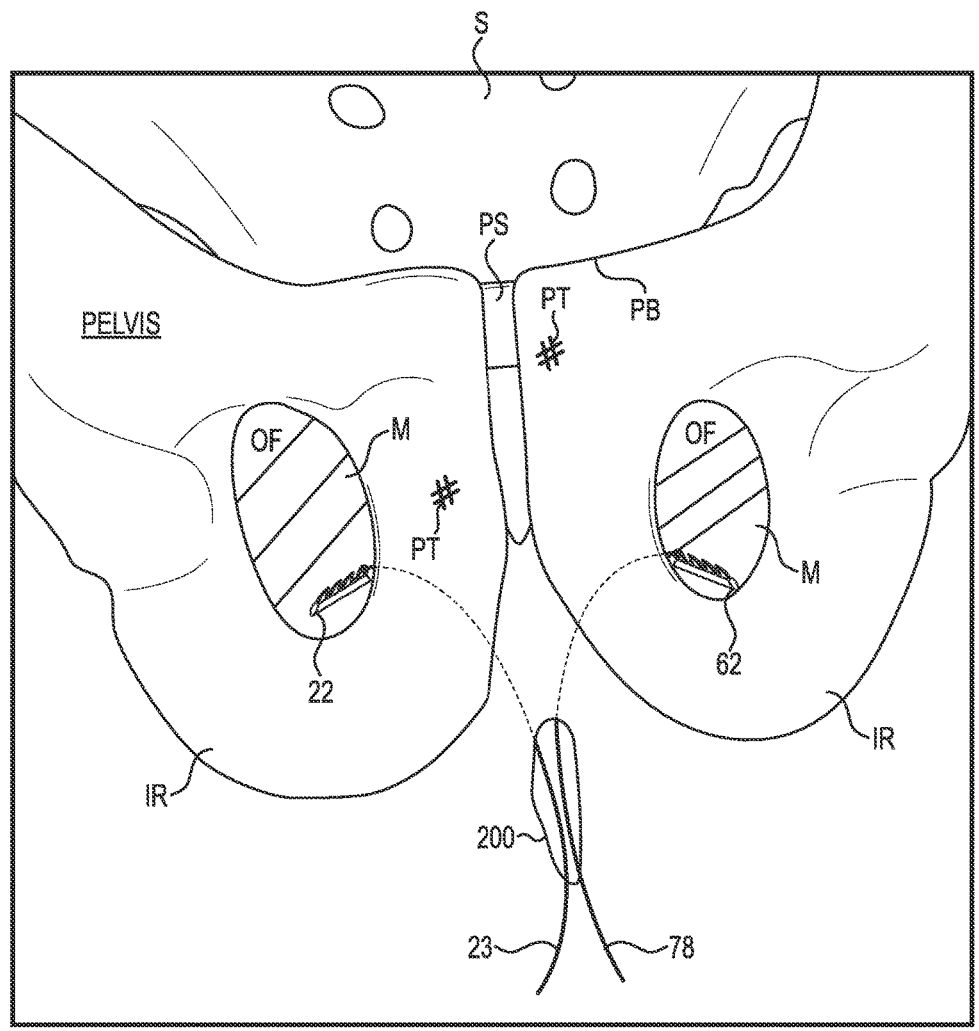

FIG. 27 is a schematic view after the surgeon completes the process described in FIGS. 24-26 on the contralateral side. The cannula 40 of the introducer 24 has been directed along the trans-obturator TO path posterior to the ramus IR until the anchor 62 is positioned and inserted into the membrane M covering the obturator foramen OF. The suture 78 trails away from the anchor 62 and exits the incision 200. With this configuration, the first suture 23 is connected to the first anchor 22 that secured in a first one of the membranes M of the obturator foramen OF, and the second suture 78 is connected to the second anchor 62 that is secured in the membrane M of the opposed second obturator foramen OF. The sutures 23, 78 extend out of the incision 200 and are available to deliver the support material through the incision 200 to support the urethra or other body organ.

Figure 28:
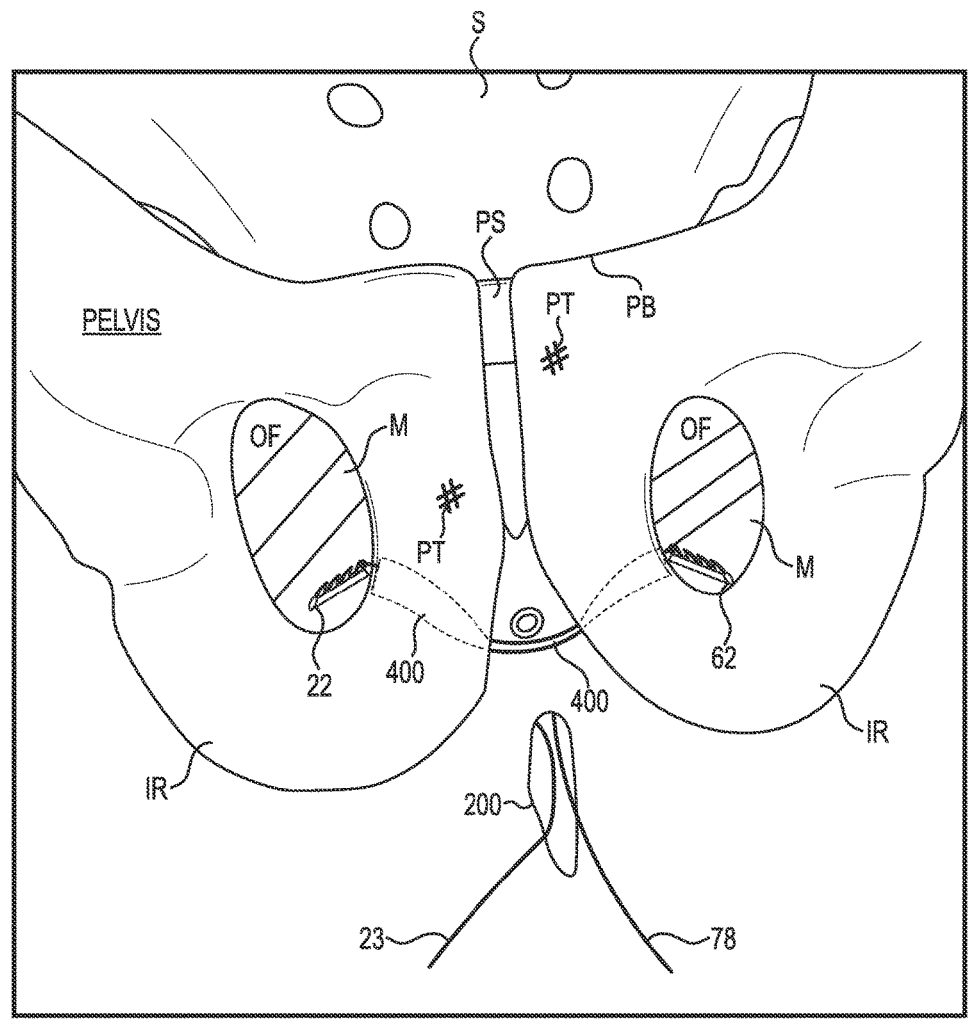

FIG. 28 is a schematic view of a support 400 inserted into a patient. A first end of the support 400 has been engaged with and delivered along the entire length of the first suture 23 to the anchor 22. A second end of the support 400 has been engaged with and delivered along the entire length of the second suture 78 up to the second anchor 62. The support 400 thus extends like a hammock from the first anchor 22 in the first membrane M of the first obturator foramen OF across the midline of the patient to the second anchor 62 in the second membrane M of the second obturator foramen OF. The surgeon terminates the first suture 23 at the support 400, for example by tying a knot, and likewise terminates the second suture 78 at the support 400. The excess length of suture 23, 78 is removed and the incision 200 is closed.

Figure 29:
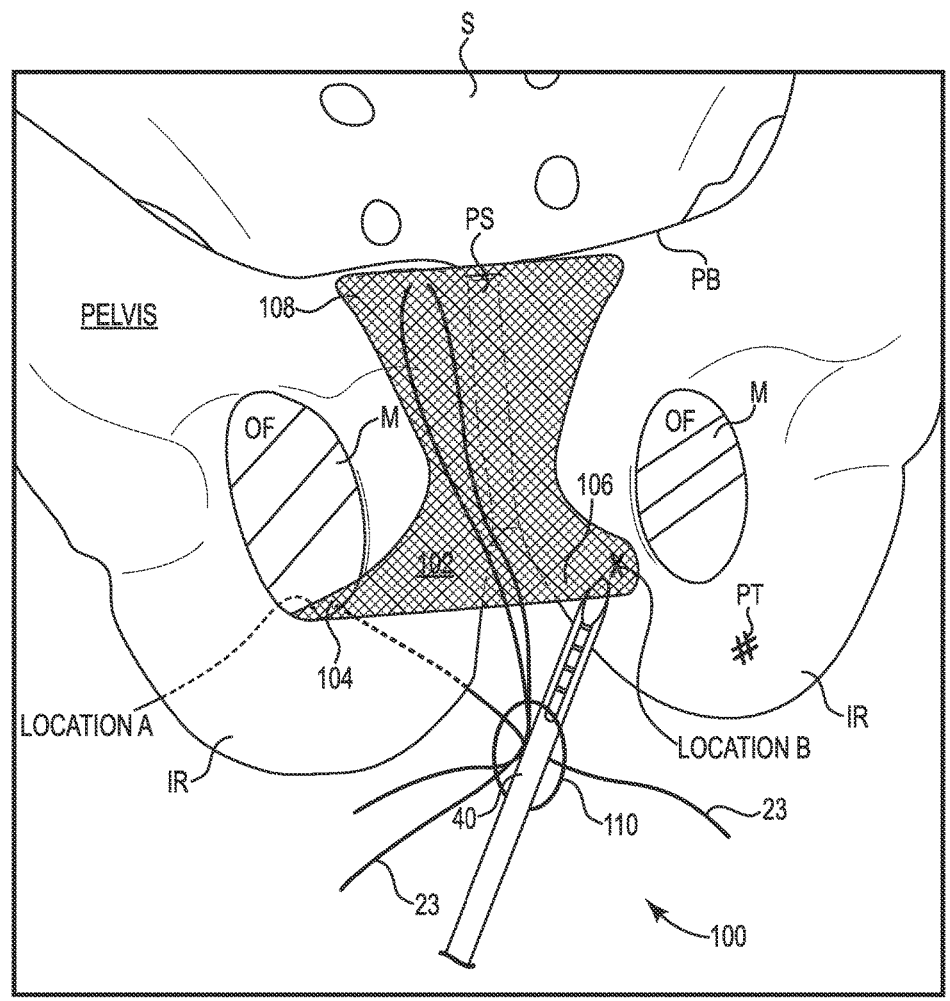
FIG. 29 is a schematic view illustrating embodiments of methods of anchoring a support to the pelvis of a male patient.

FIG. 29 is a schematic view illustrating embodiments of methods of anchoring the support 100 to the pelvis of a male patient. The pre-pubic side 108 of the support 100 is anchored at a superior location of the pelvis to the periosteum tissue anterior the pubic bone PB. The arms 104, 106 of the support 100 are suitably anchored to the periosteum tissue PT of the inferior ischial pubic ramus IR (anterior or posterior) or to the membrane M of the pelvis.

The method includes elevating and compressing the bulbar urethra of the male patient and includes:

forming a perineal incision 110 in the male patient;

inserting a first arm 104 located on a first side of the support 100 into the perineal incision 110, directing an end portion of the first arm 104 toward an obturator foramen OF of the pelvis, and fixing the end portion of the first arm 104 to either Location A) the membrane M of the obturator foramen OF or Location B) the periosteum tissue of the ramus IR adjacent to the obturator foramen OF; and inserting a second arm 106 located on a second side of the support 100 into the perineal incision 110, directing an end of the second arm 106 toward a second obturator foramen OF of the pelvis, and fixing the end portion of the second arm 106 to one of C) the membrane M of the second obturator foramen OF or D) the periosteum tissue of the ramus IR adjacent to the second obturator foramen OF; and inserting a pre-pubic side 108 of the support 100 into the perineal incision 110 and directing the pre-pubic side 108 of the support 100 anterior to the pelvis towards a pubic bone PB of the pelvis; and pushing the anchor 22 (see FIG. 2A) through the pre-pubic side 108 of the support 100 and into periosteum tissue PT over the pubic bone PB and engaging the spine portion 34 of the anchor 22 in the periosteum tissue PT of the pubic bone PB; and securing the pre-pubic side 108 of the support 100 against the periosteum tissue PT of the pubic bone PB.

The arms 104, 106 of the support 100 are suitably anchored to the periosteum tissue PT posterior to (i.e., behind) the ischial ramus IR or anterior to the ischial ramus IR. Mindful of this, and as examples, FIG. 29 illustrates the arm 104 anchored to the membrane M at a posterior location relative to the ischial ramus IR (Location A) and the arm 106 anchored to the anterior surface of the ischial ramus IR (Location B). It is suitable to attach either arm 104, 106 to the inferior edge of the ischial pubic ramus IR.

An addition to the method of anchoring the support 100 relative to the pelvis includes: inserting a body portion 30 (see FIG. 3) of the anchor 22 into a lumen 46 in a cannula 40 and having the spine portion 34 of the anchor 22 extending radially out of a wall 90 of the cannula 40; inserting a leading end 40 of the cannula 40 and the anchor 22 into the perineal incision 110; and pushing the leading end 44 of the cannula 40 and the anchor 22 into the periosteum tissue PT of the pubic bone PB.

An addition to the method of anchoring the support 100 relative to the pelvis includes: leaving a suture 23 attached to the anchor 22 trailing from the anchor 22 and out of the perineal incision 110; and tying the suture 23 against the pre-pubic 108 side of the support 100 and fixing the pre-pubic side 108 of the support 100 against the periosteum tissue PT of the pubic bone PB.

With reference to FIGS. 7 and 29, an addition to the method of anchoring the support 100 relative to the pelvis includes: leaving the suture 23 attached to the anchor 22 trailing from the anchor 22 and out of the perineal incision 110; and sliding a stopper 150 attached to the suture 23 from the perineal incision 110 inward toward the pubic bone PB and fixing the pre-pubic side 108 of the support 100 against the periosteum tissue PT and between the stopper 150 and the pubic bone PB.

An addition to the method of anchoring the support 100 relative to the pelvis includes: inserting a body portion 30 (FIG. 3) of the anchor 22 into a lumen 46 in a cannula 40 and having the spine portion 34 of the anchor 22 extending radially out of a wall 90 of the cannula 40; inserting a leading end 44 of the cannula 40 and the anchor 22 into the perineal incision 110; pushing the leading end 44 of the cannula 40 and the anchor 22 into the membrane M of the first obturator foramen OF; and fixing the end portion of the first arm 104 to the membrane M of the first obturator foramen OF.

An addition to the method of anchoring the support 100 relative to the pelvis includes: inserting a body portion 30 (FIG. 3) of the anchor 22 into a lumen 46 in a cannula 40 and having the spine portion 34 of the anchor 22 extending radially out of a wall 90 of the cannula 40; inserting a leading end 44 of the cannula 40 and the anchor 22 into the perineal incision 110; pushing the leading end 44 of the cannula 40 and the anchor 22 into the periosteum tissue PT of the ramus IR adjacent to the first obturator foramen OF; and fixing the end portion of the first arm 104 to the periosteum tissue PT of the ramus IR adjacent to the first obturator foramen OF.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention is limited only by its claims and their equivalents.

What is claimed is:

1. A method of anchoring a support material to tissue, the method comprising:
   forming an incision in a urogenital triangle of a patient for access to a pelvis of the patient;
   inserting a body portion of an anchor into a lumen in a cannula and having a spine portion of the anchor extending radially out of a wall of the cannula, where the anchor has a suture connected to the anchor with a body portion of the suture trailing away from the anchor;
   inserting a leading end of the cannula and the anchor into the incision;
   pushing the leading end of the cannula into periosteum tissue of the pelvis and engaging the spine portion of the anchor with the periosteum tissue;
   withdrawing the leading end of the cannula from the incision and leaving the anchor engaged in the periosteum tissue with the body portion of the suture extending from the anchor, through the incision, to a location exterior of the patient;
   securing the support material to the suture that is attached to the anchor; and
   delivering the support material over and along the suture from the location exterior of the patient, through the incision, and to the pelvis of the patient.

2. The method of claim 1, wherein the suture is attached to an eyelet of the anchor, the method further comprising:
   having the eyelet extending radially out of the wall of the cannula; and
   engaging the eyelet with the periosteum tissue.

3. The method of claim 1, wherein the support material is located between the anchor engaged in the periosteum tissue and a stopper that is coupled to the suture, the method further comprising:
   sliding the stopper and the support material along the suture and cinching the support material between the periosteum tissue and the stopper.

4. The method of claim 1, wherein the support material is located between the anchor engaged in the periosteum tissue and a stopper that is coupled to the suture, the method further comprising:
   tying a slip knot in the suture such that the stopper is between the slip knot and the support material;
   sliding the slip knot and the stopper and the support material along the suture to the periosteum tissue; and
   securing the support material between the periosteum tissue and the stopper.

5. The method of claim 1, further comprising:
   forming a vaginal incision in a female patient;
   inserting the leading end of the cannula and the anchor into the vaginal incision;
   pushing the leading end of the cannula into the periosteum tissue of a first ramus of the pelvis and engaging the spine portion of the anchor with the periosteum tissue of the first ramus of the pelvis and leaving the suture trailing from the anchor and out of the vaginal incision;
   withdrawing the cannula out of the vaginal incision;
   inserting a second anchor into the cannula;
   pushing the leading end of the cannula into periosteum tissue of a second ramus of the pelvis and engaging a spine portion of the second anchor with the periosteum tissue of the second ramus of the pelvis and leaving a second suture trailing from the second anchor and out of the vaginal incision;
   delivering a first end portion of a sling along the first suture and through the vaginal incision and to the first ramus of the pelvis;
   delivering a second end portion of the sling along the second suture and through the vaginal incision and to the second ramus of the pelvis; and
   securing the first suture to the first end portion of the sling and securing the second suture to the second end portion of the sling.

6. The method of claim 1, further comprising:
   inserting a support into the incision with the support extending from a first ramus across a midline of the patient to a second ramus;
   pushing the spine portion of the anchor through a first end portion of the support and into the periosteum tissue associated with the first ramus and leaving a first suture segment extending through the first end portion of the support and through the incision;

loading a body portion of a second anchor into a second lumen formed in a second cannula with a spine portion of the second anchor extending radially out of a wall in the second cannula;

guiding the second cannula through the incision;

pushing the spine portion of the second anchor through a second end portion of the support and into the periosteum tissue associated with the second ramus and leaving a second suture segment extending through the second end portion of the support and through the incision; and pulling a free end of the suture connected to both of the first suture segment and the second suture segment and securing the first end portion of the support to the first ramus and securing the second end portion of the support to the second ramus.

7. The method of claim 6, further comprising:

a stopper coupled in sliding arrangement to the first suture segment and the second suture segment; and sliding the stopper along the suture, securing the stopper against the support, and taking slack out of the suture.

8. The method of claim 7, wherein the stopper has a first orifice and a second orifice, with the first segment of the suture inserted through the first orifice and the second segment of the suture and the free end of the suture inserted through the second orifice.

9. The method of claim 1, comprising inserting the body portion of the anchor and a portion of the spine portion of the anchor into the lumen in the cannula.

10. The method of claim 1, comprising inserting the body portion of the anchor and a portion of the spine portion of the anchor into the lumen in the cannula and having part of the spine portion of the anchor extending radially out of the lumen and through the wall of the cannula.

11. The method of claim 1, comprising pushing the leading end of the cannula into periosteum tissue of the pelvis and engaging the spine portion of the anchor with the periosteum tissue without the cannula penetrating the bone.

12. The method of claim 1, comprising pushing the leading end of the cannula into periosteum tissue of the pelvis and engaging the spine portion of the anchor with the periosteum tissue without the anchor penetrating the bone.

13. The method of claim 1, comprising pushing the leading end of the cannula into periosteum tissue of the pelvis and engaging the spine portion of the anchor with the periosteum tissue without the spine portion of the anchor penetrating the bone.

14. The method of claim 1, comprising forming the incision in the urogenital triangle of a female patient for access to the pelvis of the female patient.

15. A method of anchoring a support material to tissue, the method comprising:

forming an incision in a urogenital triangle of a patient for access to a pelvis of the patient;

inserting an anchor into a lumen in a cannula with a spine portion of the anchor extending radially out of a wall of the cannula and a suture connected to the anchor having a suture body trailing away from the anchor and the cannula;

inserting a leading end of the cannula and the anchor into the incision;

pushing the leading end of the cannula into periosteum tissue of the pelvis and engaging the spine portion of the anchor with the periosteum tissue;

withdrawing the leading end of the cannula from the incision and leaving the suture body extending from the anchor, through the incision, to a location exterior of the patient;

placing the suture through the support material; and sliding the support material over and along the suture body from the location exterior of the patient, through the incision, and to the pelvis of the patient.

16. The method of claim 15, further comprising:

sliding a stopper and the support material over and along the suture body and securing the support material between the periosteum tissue and the stopper.

17. The method of claim 15, further comprising:

tying a slip knot in the suture;

sliding the slip knot and the support material along the suture body towards the periosteum tissue; and securing the support material between the periosteum tissue and the slip knot.

* * * * *